United States Patent
Takamatsu et al.

(10) Patent No.: US 8,940,926 B2
(45) Date of Patent: Jan. 27, 2015

(54) METHOD FOR PRODUCING CARBAMATE, METHOD FOR PRODUCING ISOCYANATE, CARBAMATE PRODUCTION SYSTEM, AND ISOCYANATE PRODUCTION SYSTEM

(75) Inventors: Koji Takamatsu, Takaishi (JP); Satoshi Kato, Kashima (JP); Takeshi Fukuda, Kurume (JP); Tetsuya Nakano, Sakai (JP); Masaaki Sasaki, Ichihara (JP)

(73) Assignee: Mitsui Chemicals, Inc., Tokyo (JP)

( * ) Notice: Subject to any disclaimer, the term of this patent is extended or adjusted under 35 U.S.C. 154(b) by 113 days.

(21) Appl. No.: 13/701,980

(22) PCT Filed: May 19, 2011

(86) PCT No.: PCT/JP2011/061515
§ 371 (c)(1),
(2), (4) Date: Dec. 4, 2012

(87) PCT Pub. No.: WO2011/158598
PCT Pub. Date: Dec. 22, 2011

(65) Prior Publication Data
US 2013/0079546 A1    Mar. 28, 2013

(30) Foreign Application Priority Data

Jun. 16, 2010  (JP) ................................. 2010-137642
Jun. 16, 2010  (JP) ................................. 2010-137643

(51) Int. Cl.
*C07C 263/00*   (2006.01)
*C07C 261/00*   (2006.01)
*C07C 263/04*   (2006.01)
(Continued)

(52) U.S. Cl.
CPC ............. *C07C 263/04* (2013.01); *C07C 269/04* (2013.01); *C07C 273/04* (2013.01)

USPC ............................................. 560/345; 560/24

(58) Field of Classification Search
None
See application file for complete search history.

(56) References Cited

U.S. PATENT DOCUMENTS

| 5,427,759 A | 6/1995 | Heitmann et al. |
| 2001/0005761 A1 | 6/2001 | Laqua et al. |

(Continued)

FOREIGN PATENT DOCUMENTS

| CN | 1201450 | 12/1998 |
| CN | 1546464 | 11/2004 |

(Continued)

OTHER PUBLICATIONS

International Search Report PCT/JP2011/061515 dated Aug. 2, 2011.

(Continued)

*Primary Examiner* — Karl J Puttlitz
(74) *Attorney, Agent, or Firm* — Foley & Lardner LLP

(57) ABSTRACT

A method for producing carbamate including a urea production step; a carbamate-forming step; an ammonia separation step of absorbing the gas with water in the presence of carbonate to produce a gas absorption water, and separating ammonia; an aqueous alcohol solution separation step of separating an aqueous alcohol solution from the gas absorption water; an ammonia/carbon dioxide separation step of separating carbon dioxide gas from the aqueous ammonia solution in the gas absorption water from which the aqueous alcohol solution is separated; an aqueous ammonia solution reusing step of mixing the aqueous ammonia solution and carbonate with the water to be used for production of the gas absorption water.

7 Claims, 3 Drawing Sheets

(51) Int. Cl.
*C07C 269/04* (2006.01)
*C07C 273/04* (2006.01)

(56) References Cited

U.S. PATENT DOCUMENTS

| | | | |
|---|---|---|---|
| 2002/0002905 A1 | 1/2002 | Umino et al. | |
| 2009/0275775 A1* | 11/2009 | Kloetzer et al. | 560/344 |
| 2010/0274046 A1 | 10/2010 | Kloetzer et al. | |

FOREIGN PATENT DOCUMENTS

| | | |
|---|---|---|
| CN | 101374802 | 2/2009 |
| EP | 2 439 191 | 4/2012 |
| JP | 6-115928 | 4/1994 |
| JP | 07-157463 | 6/1995 |
| JP | 08-277255 | 10/1996 |
| JP | 2001-316110 | 11/2001 |
| JP | 2010-501615 | 1/2010 |
| WO | WO 2010/116871 A1 | 10/2010 |
| WO | WO 2011/021257 A1 | 2/2011 |

OTHER PUBLICATIONS

Office Action for Chinese Application No. 201180024326.2 dated Sep. 10, 2013.

* cited by examiner

METHOD FOR PRODUCING CARBAMATE, METHOD FOR PRODUCING ISOCYANATE, CARBAMATE PRODUCTION SYSTEM, AND ISOCYANATE PRODUCTION SYSTEM

TECHNICAL FIELD

The present invention relates to a method for producing carbamate, a method for producing isocyanate, a carbamate production system, and an isocyanate production system.

BACKGROUND ART

Isocyanate is an organic compound having at least one isocyanate group (—NCO), and is widely used industrially as a raw material for polyurethane, polyurea, etc.

Conventionally, isocyanate has been industrially produced by reaction between amine and phosgene (phosgene method). However, phosgene has various problems such as being highly toxic and troublesome in handling, and requiring careful attention to corrosion of the equipment because it by-produces a large amount of hydrochloric acid. Accordingly, there is a need to develop industrial production methods for isocyanate that can replace the phosgene method.

Known isocyanate production methods that do not use phosgene include a method (urea method) in which amine, urea and/or N-unsubstituted carbamic acid ester, and alcohol are allowed to react (carbamate-forming reaction), and thereafter the obtained carbamate is thermally decomposed.

Meanwhile, it has been known that the carbamate-forming reaction in the urea method by-produces ammonia and carbon dioxide.

Ammonia and carbon dioxide can be used, for example, for production of urea, a raw material component of carbamate-forming reaction, and therefore industrially, it is desired to recover the by-produced ammonia and carbon dioxide, and effectively utilize them.

As a method for producing carbamate in which ammonia is recovered, for example, Patent Document 1 below has proposed a method in which a drained gas containing an organic component, carbon dioxide, and ammonia is washed with an alkaline solution (e.g., caustic soda solution, etc.) to remove organic components and carbon dioxide, and at the same time, to distill ammonia as an overhead product (for example, see Patent Document 1 below).

CITATION LIST

Patent Document

Patent Document 1
Japanese Unexamined Patent Publication No. Hei 6-115928

SUMMARY OF THE INVENTION

Problem to be Solved by the Invention

However, in the above-described method, although ammonia can be recovered, carbon dioxide is drained as alkaline carbonate (e.g., sodium carbonate, etc.), and therefore the alkaline solution (e.g., caustic soda solution, etc.) has to be fed continuously. Thus, the method is disadvantageous in terms of costs.

An object of the present invention is to provide a method for producing carbamate and a carbamate production system, in which the by-product in carbamate-forming reaction is efficiently recovered and is effectively utilized; and to a method for producing isocyanate and an isocyanate production system that can produce industrially useful isocyanate by using the carbamate obtained in the method for producing carbamate and the carbamate production system.

Means for Solving the Problem

To achieve the above object, a method for producing carbamate of the present invention includes
a urea production step of producing urea by reaction between ammonia and carbon dioxide gas;
a carbamate-forming step of producing carbamate by carbamate-forming reaction between amine, the urea, and alcohol, and by-producing a gas containing alcohol, ammonia, and carbon dioxide;
an ammonia separation step of absorbing the gas with water, to produce a gas absorption water, and separating ammonia;
an aqueous alcohol solution separation step of separating an aqueous alcohol solution from the gas absorption water;
an ammonia/carbon dioxide separation step of separating carbon dioxide gas from an aqueous ammonia solution in the gas absorption water from which the aqueous alcohol solution is separated; and
an aqueous ammonia solution reusing step of using the aqueous ammonia solution along with the water for production of the gas absorption water.

In the method for producing carbamate of the present invention, it is preferable that in the ammonia separation step, the gas is absorbed with the water in the presence of carbonate; in the ammonia/carbon dioxide separation step, carbon dioxide gas is separated from the aqueous ammonia solution in the presence of the carbonate; and in the aqueous ammonia solution reusing step, along with the aqueous ammonia solution and the water, the carbonate is used for production of the gas absorption water.

In the method for producing carbamate of the present invention, it is preferable that the method further includes a carbon dioxide gas reusing step in which carbon dioxide gas separated in the ammonia/carbon dioxide separation step is recovered and used in the urea production step.

In the method for producing carbamate of the present invention, it is preferable that the method further includes an ammonia reusing step in which the ammonia separated in the ammonia separation step is used in the urea production step.

In the method for producing carbamate of the present invention, it is preferable that the method further includes an alcohol reusing step in which the alcohol is separated from the aqueous alcohol solution and used in the carbamate-forming step.

In the method for producing carbamate of the present invention, it is preferable that the method further includes a water reusing step in which water drained in the urea production step is used in the ammonia separation step.

A method for producing carbamate of the present invention includes a urea production step of producing urea by reaction between ammonia and carbon dioxide gas; a carbamate-forming step of producing carbamate by carbamate-forming reaction between amine, the urea, and alcohol, and by-producing a gas containing alcohol, ammonia, and carbon dioxide; an ammonia separation step of absorbing the gas with water to produce a gas absorption water, and separating ammonia; an aqueous alcohol solution separation step of separating an aqueous alcohol solution from the gas absorption water; and an ammonium carbonate reusing step of using, in the urea production step, an aqueous ammonium carbonate solution obtained by separation of the aqueous alcohol solution from the gas absorption water.

In the method for producing carbamate of the present invention, it is preferable that the method further includes an ammonia reusing step of using, in the urea production step, the ammonia separated in the ammonia separation step.

In the method for producing carbamate of the present invention, it is preferable that the method further includes an alcohol reusing step of separating alcohol from the aqueous alcohol solution and using the alcohol in the carbamate-forming step.

In the method for producing carbamate of the present invention, it is preferable that the method further includes a water reusing step of using, in the ammonia separation step, water drained in urea production step.

A method for producing isocyanate of the present invention includes a carbamate production step of producing carbamate by a method for producing carbamate, and an isocyanate production step of producing isocyanate by thermally decomposing the obtained carbamate,
the method for producing carbamate including the steps of:
a urea production step of producing urea by reaction between ammonia and carbon dioxide gas,
a carbamate-forming step of producing carbamate by carbamate-forming reaction between amine, the urea, and alcohol, and by-producing a gas containing alcohol, ammonia, and carbon dioxide,
an ammonia separation step of absorbing the gas with water to produce a gas absorption water, and separating ammonia,
an aqueous alcohol solution separation step of separating an aqueous alcohol solution from the gas absorption water,
an ammonia/carbon dioxide separation step of separating carbon dioxide gas from the aqueous ammonia solution in the gas absorption water in which the aqueous alcohol solution is separated, and
an aqueous ammonia solution reusing step of using the aqueous ammonia solution along with the water for production of the gas absorption water.

A method for producing isocyanate of the present invention includes a carbamate production step of producing carbamate by a method for producing carbamate, and
an isocyanate production step of producing isocyanate by thermally decomposing the obtained carbamate, the method for producing carbamate including
a urea production step of producing urea by reaction between ammonia and carbon dioxide gas,
a carbamate-forming step of producing carbamate by carbamate-forming reaction between amine, the urea, and alcohol, and by-producing a gas containing alcohol, ammonia, and carbon dioxide,
an ammonia separation step of absorbing the gas with water to produce a gas absorption water, and separating ammonia,
an aqueous alcohol solution separation step of separating an aqueous alcohol solution from the gas absorption water, and
an ammonium carbonate reusing step of using, in the urea production step, an aqueous ammonium carbonate solution obtained by separating the aqueous alcohol solution from the gas absorption water.

A carbamate production system of the present invention includes
a urea production apparatus for producing urea by reaction between ammonia and carbon dioxide gas;
a carbamate-forming reaction apparatus for producing carbamate by carbamate-forming reaction between amine, the urea, and alcohol, and by-producing a gas containing alcohol, ammonia, and carbon dioxide;
an ammonia separation apparatus for absorbing the gas with water to produce a gas absorption water, and separating ammonia;
an aqueous alcohol solution separation apparatus for separating an aqueous alcohol solution from the gas absorption water;
an ammonia/carbon dioxide separation apparatus for separating carbon dioxide gas from an aqueous ammonia solution in the gas absorption water from which the aqueous alcohol solution is separated;
an aqueous ammonia solution reusing apparatus for using the aqueous ammonia solution along with the water for production of the gas absorption water;
an ammonia reusing apparatus for using the ammonia separated in the ammonia separation apparatus in the urea production apparatus; and
an alcohol reusing apparatus for separating alcohol from an aqueous alcohol solution and using the alcohol in the carbamate-forming reaction apparatus.

A carbamate production system of the present invention includes
a urea production apparatus for producing urea by reaction between ammonia and carbon dioxide gas;
a carbamate-forming reaction apparatus for producing carbamate by carbamate-forming reaction between amine, the urea, and alcohol, and by-producing a gas containing alcohol, ammonia, and carbon dioxide;
an ammonia separation apparatus for absorbing the gas with water to produce a gas absorption water, and separating ammonia;
an aqueous alcohol solution separation apparatus for separating an aqueous alcohol solution from the gas absorption water;
an ammonium carbonate reusing apparatus for using, in the urea production apparatus, an aqueous ammonium carbonate solution obtained by separation of the aqueous alcohol solution from the gas absorption water;
an ammonia reusing apparatus for using, in the urea production apparatus, the ammonia separated in the ammonia separation apparatus; and
an alcohol reusing apparatus for separating alcohol from the aqueous alcohol solution and using the alcohol in the carbamate-forming reaction apparatus.

An isocyanate production system of the present invention includes a carbamate production system, and a thermal decomposition apparatus for thermally decomposing the carbamate obtained in the carbamate production system to produce isocyanate, the carbamate production system including
a urea production apparatus for producing urea by reaction between ammonia and carbon dioxide gas;
a carbamate-forming reaction apparatus for producing carbamate by carbamate-forming reaction between amine, the urea, and alcohol, and by-producing a gas containing alcohol, ammonia, and carbon dioxide;
an ammonia separation apparatus for absorbing the gas with water to produce a gas absorption water, and separating ammonia;
an aqueous alcohol solution separation apparatus for separating an aqueous alcohol solution from the gas absorption water;
an ammonia/carbon dioxide separation apparatus for separating carbon dioxide gas from the aqueous ammonia solution in the gas absorption water from which the aqueous alcohol solution is separated;

an aqueous ammonia solution reusing apparatus for using the aqueous ammonia solution along with the water for production of the gas absorption water;

an ammonia reusing apparatus for using, in the urea production apparatus, the ammonia separated in the ammonia separation apparatus; and an alcohol reusing apparatus for separating alcohol from the aqueous alcohol solution and using the alcohol in the carbamate-forming reaction apparatus.

An isocyanate production system of the present invention includes a carbamate production system, and a thermal decomposition apparatus for thermally decomposing the obtained carbamate in the carbamate production system to produce isocyanate, the carbamate production system including a urea production apparatus for producing urea by reaction between ammonia and carbon dioxide gas;

a carbamate-forming reaction apparatus for producing carbamate by carbamate-forming reaction between amine, the urea, and alcohol, and by-producing a gas containing alcohol, ammonia, and carbon dioxide;

an ammonia separation apparatus for absorbing the gas with water to produce a gas absorption water, and separating ammonia;

an aqueous alcohol solution separation apparatus for separating an aqueous alcohol solution from the gas absorption water;

an ammonium carbonate reusing apparatus for using, in the urea production apparatus, an aqueous ammonium carbonate solution obtained by separating the aqueous alcohol solution from the gas absorption water;

an ammonia reusing apparatus for using, in the urea production apparatus, the ammonia separated in the ammonia separation apparatus; and an alcohol reusing apparatus for separating alcohol from an aqueous alcohol solution and using the alcohol in the carbamate-forming reaction apparatus.

Effects of the Invention

With a method for producing carbamate of the present invention and a production system thereof, a gas containing alcohol, ammonia, and carbon dioxide obtained from carbamate-forming reaction is absorbed with water, and therefore alkaline carbonate is not produced in the gas absorption water, and therefore ammonia in the gas absorption water can be recovered and reused.

Thus, with the method for producing carbamate of the present invention and the production system thereof, by-products of carbamate-forming reaction can be efficiently recovered and effectively utilized, and furthermore, waste components can be reduced; therefore, the method and the system is advantageous in costs.

With a method for producing isocyanate of the present invention and a production system thereof, isocyanate, which is industrially useful as a raw material for polyurethane, can be produced at low costs and efficiently.

DESCRIPTION OF EMBODIMENTS

Figure 1:
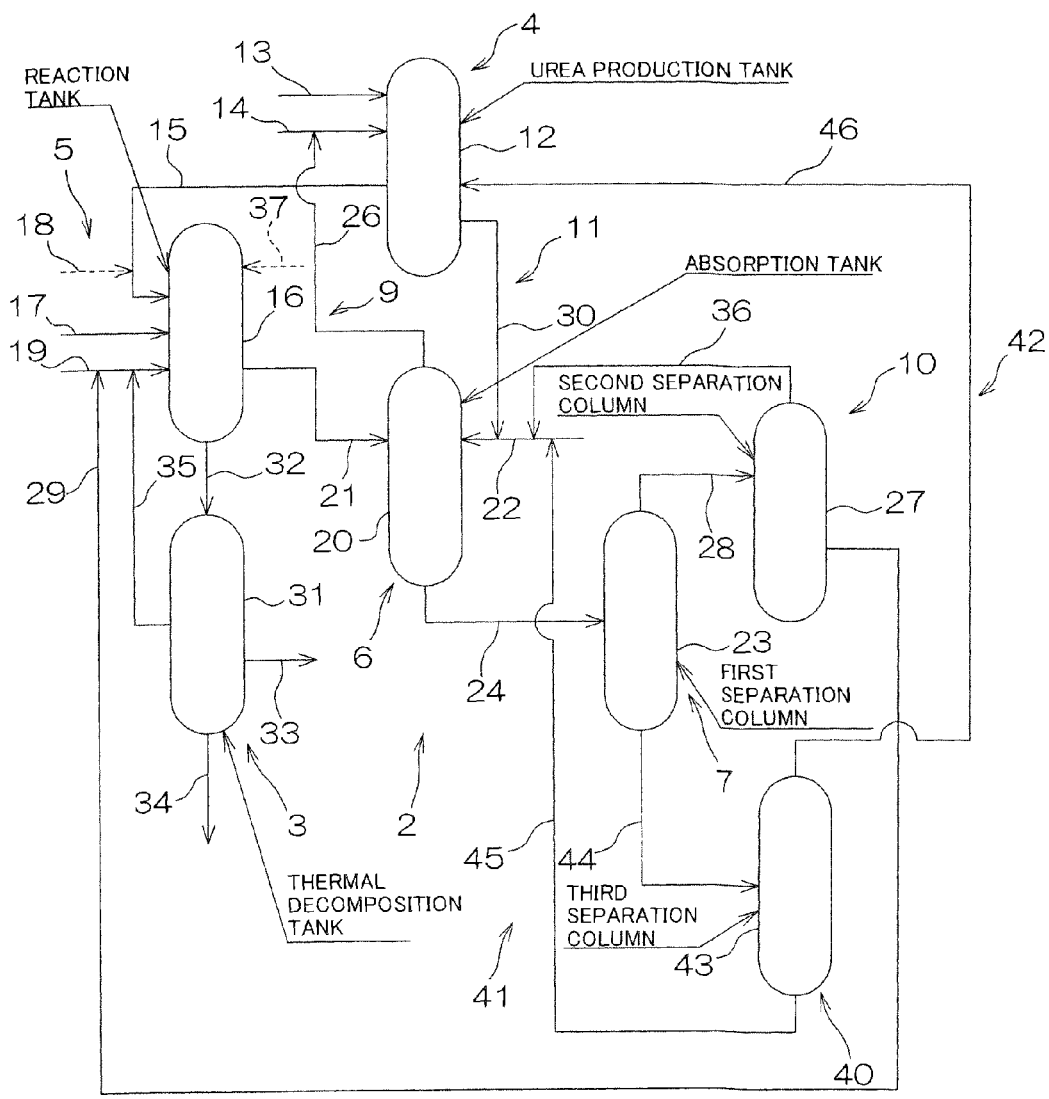
FIG. 1 is a schematic diagram illustrating the configuration of a first embodiment of a plant as a carbamate production system and an isocyanate production system in which a method for producing carbamate and a method for producing isocyanate of the present invention are used.

First, a method for producing carbamate of the present invention is described. In the method for producing carbamate of the present invention, first, urea is produced by reaction between ammonia and carbon dioxide gas (urea production step).

To produce urea, industrially, for example, first, as shown in the formula (1) below, ammonia is allowed to react with carbon dioxide (carbon dioxide gas), thereby producing ammonium carbamate.

$$2NH_3 + CO_2 \rightarrow NH_2COONH_4 \tag{1}$$

Reaction between ammonia and carbon dioxide can be performed by a known method, and the reaction conditions thereof (mixing formulation, temperature, pressure, etc.) are set suitably in accordance with purpose and application.

Next, in this method, as shown in the formula (2) below, the obtained ammonium carbamate is subjected to dehydration, thereby decomposing the ammonium carbamate into urea and water.

$$NH_2COONH_4 \rightarrow NH_2CONH_2 + H_2O \tag{2}$$

The dehydration of ammonium carbamate can be performed by a known method, and the reaction conditions thereof (temperature, pressure, etc.) are set suitably in accordance with purpose and application.

The water by-produced (drained) in the above-described dehydration is, although to be described later, preferably, used in an ammonia separation step (described later) to absorb gas (described later) (water reusing step (described later)).

Next, in this method, carbamate is produced by carbamate-forming reaction of urea obtained as described above, amine, and alcohol, and furthermore, although to be described later, a gas containing alcohol, ammonia, and carbon dioxide (described later) is by-produced (carbamate-forming step).

Examples of the amine include primary amines.

Primary amines are amino group-containing organic compounds having one or more primary amino group, and for example, represented by the general formula (3) below.

$$R^1-(NH_2)n \tag{3}$$

(where $R^1$ represents an aliphatic hydrocarbon group having 1 to 15 carbon atoms in total, an alicyclic ring-containing hydrocarbon group having 3 to 15 carbon atoms in total, or an aromatic ring-containing hydrocarbon group having 6 to 15 carbon atoms in total; and n represents an integer of 1 to 6.)

In the above-described formula (3), $R^1$ is selected from an aliphatic hydrocarbon group having 1 to 15 carbon atoms in total, an alicyclic ring-containing hydrocarbon group having 3 to 15 carbon atoms in total, and an aromatic ring-containing hydrocarbon group having 6 to 15 carbon atoms in total. $R^1$ may contain, in its hydrocarbon group, for example, stable linkages such as an ether linkage, a thioether linkage, and an ester linkage, and may be replaced with a stable functional group (described later).

In $R^1$, examples of the aliphatic hydrocarbon group having 1 to 15 carbon atoms in total include a monovalent to hexavalent linear or branched aliphatic hydrocarbon group having 1 to 15 carbon atoms in total.

In the formula (3) above, examples of $R^1$ as the primary amine of an aliphatic hydrocarbon group having 1 to 15 carbon atoms in total include an aliphatic amine having 1 to 15 carbon atoms in total.

Examples of such aliphatic amines include linear or branched aliphatic primary monoamines such as methylamine, ethylamine, n-propylamine, iso-propylamine, butylamine, pentylamine, hexylamine, n-octylamine, 2-ethylhexylamine, decylamine, dodecylamine, and tetradecylamine; aliphatic primary diamines such as 1,2-diaminoethane, 1,3-diaminopropane, 1,4-diaminobutane (1,4-tetramethylenediamine), 1,5-diaminopentane (1,5-pentamethylenediamine), 1,6-diaminohexane (1,6-hexamethylenediamine), 1,7-diaminoheptane, 1,8-diaminooctane, 1,9-diaminononane, 1,10-diaminodecane, 1,12-diaminododecane, 2,2,4-trimethylhexamethylenediamine, 2,4,4-trimethylhexamethylenediamine, and tetramethylenediamine; and aliphatic primary triamines such as 1,2,3-triaminopropane, triaminohexane, triaminononane, triaminododecane, 1,8-diamino-4-aminomethyloctane, 1,3,6-triaminohexane, 1,6,11-triaminoundecane, and 3-aminomethyl-1,6-diaminohexane.

In $R^1$, examples of the alicyclic ring-containing hydrocarbon group having 3 to 15 carbon atoms in total include a monovalent to hexavalent alicyclic ring-containing hydrocarbon group having 3 to 15 carbon atoms in total.

The alicyclic ring-containing hydrocarbon group is not limited as long as it contains one or more alicyclic ring hydrocarbon in its hydrocarbon group, and for example, an aliphatic hydrocarbon group may be bonded to the alicyclic ring hydrocarbon. In this case, the amino group in the primary amine may be bonded directly to the alicyclic ring hydrocarbon, or may be bonded to the aliphatic hydrocarbon group bonded to the alicyclic ring hydrocarbon, or may be both.

In the above-described formula (3), examples of $R^1$ as primary amine of alicyclic ring-containing hydrocarbon group having 3 to 15 carbon atoms in total include alicyclic amines having 3 to 15 carbon atoms in total.

Examples of such alicyclic amines include alicyclic primary monoamines such as cyclopropylamine, cyclobutylamine, cyclopentylamine, cyclohexylamine, and hydrogenated toluidine; alicyclic primary diamines such as diaminocyclobutane, isophoronediamine (3-aminomethyl-3,5,5-trimethylcyclohexylamine), 1,2-diaminocyclohexane, 1,3-diaminocyclohexane, 1,4-diaminocyclohexane, 1,3-bis(aminomethyl)cyclohexane, 1,4-bis(aminomethyl)cyclohexane, 4,4'-methylenebis(cyclohexylamine), 2,5-bis(aminomethyl) bicyclo[2,2,1]heptane, 2,6-bis(aminomethyl) bicyclo[2,2,1]heptane, hydrogenated 2,4-tolylenediamine, and hydrogenated 2,6-tolylenediamine; and alicyclic primary triamine such as triaminocyclohexane.

In $R^1$ examples of the aromatic ring-containing hydrocarbon group having 6 to 15 carbon atoms in total include a monovalent to hexavalent aromatic ring-containing hydrocarbon group having 6 to 15 carbon atoms in total.

The aromatic ring-containing hydrocarbon group is not limited as long as it contains one or more aromatic hydrocarbon in its hydrocarbon group, and for example, an aliphatic hydrocarbon group may be bonded to the aromatic hydrocarbon. In this case, the amino group in the primary amine may be bonded directly to the aromatic hydrocarbon, or may be bonded to the aliphatic hydrocarbon group bonded to the aromatic hydrocarbon, or may be both.

In the above-described formula (3), examples of $R^1$ as primary amine of aromatic ring-containing hydrocarbon group having 6 to 15 carbon atoms in total include aromatic amine having 6 to 15 carbon atoms in total, and aralkyl amine having 6 to 15 carbon atoms in total.

Examples of such aromatic amines include aromatic primary monoamines such as aniline, o-toluidine (2-methylaniline), m-toluidine (3-methylaniline), p-toluidine (4-methylaniline), 2,3-xylidine (2,3-dimethylaniline), 2,4-xylidine (2,4-dimethylaniline), 2,5-xylidine (2,5-dimethylaniline), 2,6-xylidine (2,6-dimethylaniline), 3,4-xylidine (3,4-dimethylaniline), 3,5-xylidine (3,5-dimethylaniline), 1-naphthylamine, and 2-naphthylamine; and aromatic primary diamines such as 2,4-tolylenediamine (2,4-diaminotoluene), 2,6-tolylenediamine (2,6-diaminotoluene), 4,4'-diphenylmethanediamine, 2,4'-diphenylmethanediamine, 2,2'-diphenylmethanediamine, 4,4'-diphenylether diamine, 2-nitrodiphenyl-4,4'-diamine, 2,2'-diphenylpropane-4,4'-diamine, 3,3'-dimethyldiphenylmethane-4,4'-diamine, 4,4'-diphenylpropane diamine, m-phenylenediamine, p-phenylenediamine, naphthylene-1,4-diamine, naphthylene-1,5-diamine, and 3,3'-dimethoxydiphenyl-4,4'-diamine.

Examples of such aralkyl amines include aralkyl primary monoamines such as benzylamine; and aralkyl primary diamines such as 1,3-bis(aminomethyl)benzene, 1,4-bis(aminomethyl)benzene, 1,3-tetramethylxylylenediamine (1,3-di(2-amino-2-methylethyl)benzene), and 1,4-tetramethylxylylenediamine (1,4-bis(2-amino-2-methylethyl)benzene).

In the above-described formula (3), examples of functional groups that $R^1$ may be replaced with include a nitro group, a hydroxyl group, a mercapto group, an oxo group, a thioxo group, a cyano group, a carboxy group, an alkoxy-carbonyl group (alkoxycarbonyl group having 2 to 4 carbon atoms in total e.g., methoxycarbonyl group, ethoxycarbonyl group), a sulfo group, halogen atoms (e.g., fluorine, chlorine, bromine, iodine, etc.), a lower alkoxy group (e.g., methoxy group, ethoxy group, propoxy group, butoxy group, iso-butoxy group, sec-butoxy group, tert-butoxy group, etc.), an aryloxy group (e.g., phenoxy group, etc.), a halogenophenoxy group (e.g., o-, m- or p-chlorophenoxy group, o-, m- or p-bromophenoxy group, etc.), a lower alkylthio group (e.g., methylthio group, an ethylthio group, an n-propylthio group, an iso-propylthio group, an n-butylthio group, a tert-butylthio group, etc.), an arylthio group (e.g., phenylthio group, etc.), a lower alkylsulfinyl group (e.g., methylsulfinyl group, ethylsulfinyl group, etc.), a lower alkylsulfonyl group (e.g., methylsulfonyl group, an ethylsulfonyl group, etc.), an arylsulfonyl group (e.g., phenylsulfonyl, etc.), a lower acyl group (e.g., formyl group, acetyl group, etc.), and an arylcarbonyl group (e.g. benzoyl group, etc.).

In the above-described formula (3), $R^1$ may be replaced with a plurality of these functional groups, and when $R^1$ is replaced with a plurality of functional groups, the functional groups may be the same or different from each other.

In the above-described formula (3), n represents, for example, an integer of 1 to 6, preferably, 1 or 2, and more preferably, 2.

These amines may be used singly or in a combination of two or more.

Examples of the amine include, preferably, in the above-described formula (3), $R^1$ as primary amine of alicyclic ring-containing hydrocarbon group having 3 to 15 carbon atoms in total, $R^1$ as primary amine of aromatic ring-containing hydrocarbon group having 6 to 15 carbon atoms in total, and to be more specific, an alicyclic amine having 3 to 15 carbon atoms in total, an aromatic amine having 6 to 15 carbon atoms in total, and an aralkyl amine having 6 to 15 carbon atoms in total.

Examples of the amine also include those amines that can be used as a production raw material of industrially used isocyanate (described later), and such primary amines include 1,5-diaminopentane, 1,6-diaminohexane, isophoronediamine, 1,3-bis(aminomethyl)cyclohexane, 1,4-bis(aminomethyl)cyclohexane, 4,4'-methylenebis(cyclohexylamine), 2,5-bis(aminomethyl) bicyclo[2,2,1]heptane, 2,6-bis(aminomethyl) bicyclo[2,2,1]heptane, 2,4-tolylenediamine (2,4-diaminotoluene), 2,6-tolylenediamine (2,6-diaminotoluene), 4,4'-diphenylmethanediamine, 2,4'-diphenylmethanediamine, 2,2'-diphenylmethanediamine, naphthylene-1,5-diamine, 1,3-bis(aminomethyl)benzene, 1,4-bis(aminomethyl)benzene, 1,3-tetramethylxylylenediamine, and 1,4-tetramethylxylylenediamine, and particularly preferably, 1,5-diaminopentane, isophoronediamine, 2,4-tolylenediamine (2,4-diaminotoluene), 2,6-tolylenediamine (2,6-diaminotoluene), 4,4'-diphenylmethanediamine, 2,4'-diphenylmethanediamine, 2,2'-diphenylmethanediamine, naphthylene-1,5-diamine, 1,3-bis(aminomethyl)benzene, 1,4-bis(aminomethyl)benzene, 1,3-tetramethylxylylenediamine, and 1,4-tetramethylxylylenediamine.

The alcohol is, for example, a primary to tertiary monohydric alcohol and is, for example, represented by the following general formula (4):

$$R^2\text{—OH} \qquad (4)$$

(where $R^2$ represents an alkyl group, or an aryl group which may have a substituent.)

In the above-described formula (4), $R^2$ represents an alkyl group, or an aryl group which may have a substituent.

Examples of the alkyl group represented by $R^2$ in the above formula (4) include: a linear or branched saturated hydrocarbon group having 1 to 8 carbon atoms such as methyl, ethyl, n-propyl, iso-propyl, n-butyl, iso-butyl, sec-butyl, tert-butyl, pentyl, hexyl, heptyl, octyl, iso-octyl, and 2-ethylhexyl; and an alicyclic saturated hydrocarbon group having 5 to 10 carbon atoms such as cyclohexyl and cyclododecyl.

As the alkyl group represented by $R^2$, it is preferable to use a linear or branched saturated hydrocarbon group having 1 to 8 carbon atoms, more preferably a linear or branched saturated hydrocarbon group having 2 to 6 carbon atoms, or even more preferably a linear saturated hydrocarbon group having 2 to 6 carbon atoms.

Examples of the alcohol in which $R^2$ represents the above-described alkyl group in the above formula (4) include: alcohols containing a linear or branched saturated hydrocarbon, such as methanol, ethanol, n-propanol, iso-propanol, n-butanol (1-butanol), iso-butanol, sec-butanol, tert-butanol, pentanol, hexanol, heptanol, octanol, iso-octanol, and 2-ethylhexanol; and alcohols containing an alicyclic saturated hydrocarbon, such as cyclohexanol and cyclododecanol.

Examples of the aryl group which may have a substituent, represented by $R^2$ in the above formula (4), include aryl groups having 6 to 18 carbon atoms such as phenyl, tolyl, xylyl, biphenyl, naphthyl, anthryl, and phenanthryl. Examples of the substituent include a hydroxyl group, a halogen atom (e.g., chlorine, fluorine, bromine, and iodine), a cyano group, an amino group, a carboxyl group, an alkoxy group (e.g., an alkoxy group having 1 to 4 carbon atoms such as a methoxy, an ethoxy, a propoxy, or a butoxy group), an aryloxy group (e.g., a phenoxy group etc.), an alkylthio group (e.g., an alkylthio group having 1 to 4 carbon atoms such as a methylthio, an ethylthio, a propylthio, or a butylthio group), and an arylthio group (e.g., a phenylthio group). When the substituents are multiply substituted at the aryl group, the substituents may be the same or different from each other.

Examples of the alcohol in which $R^2$ represents the above-described aryl group which may have a substituent in the above formula (4) include phenol, hydroxytoluene, hydroxyxylene, biphenyl alcohol, naphthalenol, anthracenol, and phenanthrenol.

These alcohols can be used alone or in a combination of two or more.

As the alcohol, in the above formula (4), it is preferable to use an alcohol in which $R^2$ represents an alkyl group, more preferably an alcohol in which $R^2$ represents an alkyl group having 1 to 8 carbon atoms, or even more preferably an alcohol in which $R^2$ represents an alkyl group having 2 to 6 carbon atoms.

As the alcohol used as a raw material component for the carbamate-forming reaction, it is preferable to include an alcohol separated from an aqueous alcohol solution to be described later.

Furthermore, other preferred examples of the alcohol used as a raw material component for the carbamate-forming reaction include an alcohol (described later) separated from the decomposition solution resulting from the thermal decomposition reaction of the carbamate.

Furthermore, in this method, as necessary, along with the above-described urea, N-unsubstituted carbamic acid ester can also be used in combination.

The N-unsubstituted carbamic acid ester is a carbamic acid ester in which a nitrogen atom of a carbamoyl group is not substituted with a functional group (i.e., the nitrogen atom is bonded to two hydrogen atoms and one carbon atom), and is represented, for example, by the following general formula (5):

$$R^2\text{O—CO—NH}_2 \qquad (5)$$

(where $R^2$ is as defined for $R^2$ in the above formula (4)).

In the above formula (5), $R^2$ is as defined for $R^2$ in the above formula (4), or in other words, represents an alkyl group, or an aryl group which may have a substituent.

Examples of the N-unsubstituted carbamic acid ester in which $R^2$ represents an alkyl group in the above formula (5) include: N-unsubstituted carbamic acid esters containing a saturated hydrocarbon such as methyl carbamate, ethyl carbamate, n-propyl carbamate, iso-propyl carbamate, n-butyl carbamate, iso-butyl carbamate, sec-butyl carbamate, tert-butyl carbamate, pentyl carbamate, hexyl carbamate, heptyl carbamate, octyl carbamate, iso-octyl carbamate, and 2-ethylhexyl carbamate; and N-unsubstituted carbamic acid esters containing an alicyclic saturated hydrocarbon such as cyclohexyl carbamate and cyclododecyl carbamate.

Examples of the N-unsubstituted carbamic acid ester in which $R^2$ represents an aryl group which may have a substituent in the above formula (5) include N-unsubstituted carbamic acid esters containing an aromatic hydrocarbon such as phenyl carbamate, tolyl carbamate, xylyl carbamate, biphenyl carbamate, naphthyl carbamate, anthryl carbamate, and phenanthryl carbamate.

These N-unsubstituted carbamic acid esters can be used alone or in a combination of two or more.

As the N-unsubstituted carbamic acid ester, it is preferable to use N-unsubstituted carbamic acid ester in which $R^2$ represents an alkyl group in the above formula (5).

In this method, the above-described amine, urea (and as necessary N-unsubstituted carbamic acid ester), and alcohol are blended, and the blended mixture is allowed to react preferably in a liquid phase.

The amounts of amine, urea (and as necessary N-unsubstituted carbamic acid ester), and alcohol are not particularly limited and can be appropriately selected over a relatively wide range.

Usually, the amount of the urea (and as necessary N-unsubstituted carbamic acid ester) and the amount of the alcohol may be equimolar or more to the amount of the amino group in the amine, so that the urea (and as necessary the N-unsubstituted carbamic acid ester), and the alcohol themselves can also be used as reaction solvents in this reaction.

When the urea (and as necessary the N-unsubstituted carbamic acid ester) and the alcohol also serve as the reaction solvents, excess amounts of the urea (and as necessary the N-unsubstituted carbamic acid ester) and the alcohol are used as required. Large excess amounts thereof, however, increase consumption energy in the separation step after the reaction, which may be unsuitable for industrial production.

Therefore, from the viewpoint of improving the yield of the carbamate, the amount(s) of the urea (and as necessary the N-unsubstituted carbamic acid ester) is/are of the order of 0.5 to 20 times moles, preferably 1 to 10 times moles, or more preferably 1 to 5 times moles with respect to one amino group of the amine, and the amount of the alcohol is of the order of 0.5 to 100 times moles, preferably 1 to 20 times moles, or more preferably 1 to 10 times moles, with respect to one amino group of the amine.

In this reaction, although a reaction solvent is not necessarily required, for example, when reaction raw materials are solid or when a reaction product is deposited, blending of a reaction solvent such as aliphatic hydrocarbons, aromatic hydrocarbons, ethers, nitriles, aliphatic halogenated hydrocarbons, amides, nitro compounds, N-methylpyrrolidinone, N,N-dimethylimidazolidinone, and dimethyl sulfoxide can improve operability.

The amount of the reaction solvent is not particularly limited as long as it is sufficient for the carbamate as a desired product to be dissolved. Industrially, the amount of the reaction solvent is preferably reduced as much as possible because it is necessary to recover the reaction solvent from the reaction solution and reduce the energy consumed for the recovery as much as possible, and also because a large amount of the reaction solvent can decrease substrate concentration on the reaction and slow the reaction rate. More specifically, the amount of the reaction solvent is usually in the range of 0 to 500 parts by mass, or preferably 0 to 100 parts by mass, per 1 part by mass of the amine.

In this reaction, the reaction temperature is appropriately selected from the range of 100 to 350° C., or preferably 150 to 300° C. When the reaction temperature is lower than this range, the reaction rate may decrease. On the other hand, when the reaction temperature is higher than this range, a side reaction increases, so that the yield of the carbamate as a desired product may be reduced.

The reaction is usually carried out under atmospheric pressure. However, when the boiling point of the component in the reaction solution is lower than the reaction temperature, the reaction may be carried out under an increased pressure or, as necessary, under a reduced pressure.

The reaction time is in the range of, for example, 0.1 to 20 hours, or preferably 0.5 to 10 hours. When the reaction time is shorter than this range, the yield of the carbamate as a desired product may be reduced. On the other hand, when it is longer than this range, the reaction is unsuitable for industrial production.

In this method, a catalyst can also be used.

There is no particular limitation on the catalyst, and examples thereof include lithium methanolate, lithium ethanolate, lithium propanolate, lithium butanolate, sodium methanolate, potassium-tert-butanolate, magnesium methanolate, calcium methanolate, tin (II) chloride, tin (IV) chloride, lead acetate, lead phosphate, antimony (III) chloride, antimony (V) chloride, aluminum acetylacetonate, aluminum-isobutylate, aluminum trichloride, bismuth (III) chloride, copper (II) acetate, copper (II) sulfate, copper (II) nitrate, bis(triphenyl-phosphinoxide)-copper (II) chloride, copper molybdate, silver acetate, gold acetate, zinc oxide, zinc chloride, zinc acetate, zinc acetonylacetate, zinc octanoate, zinc oxalate, zinc hexylate, zinc benzoate, zinc undecylenate, cerium (IV) oxide, uranyl acetate, titanium tetraisopropanolate, titanium tetrabutanolate, titanium tetrachloride, titanium tetraphenolate, titanium naphthenate, vanadium (III) chloride, vanadium acetylacetonate, chromium (III) chloride, molybdenum (VI) oxide, molybdenum acetylacetonate, tungsten (VI) oxide, manganese (II) chloride, manganese (II) acetate, manganese (III) acetate, iron (II) acetate, iron (III) acetate, iron phosphate, iron oxalate, iron (III) chloride, iron (III) bromide, cobalt acetate, cobalt chloride, cobalt sulfate, cobalt naphthenate, nickel chloride, nickel acetate, and nickel naphthenate.

Furthermore, examples of the catalyst include $Zn(OSO_2CF_3)_2$ (also known as $Zn(OTf)_2$, zinc trifluoromethanesulfonate), $Zn(OSO_2C_2F_5)_2$, $Zn(OSO_2C_3F_7)_2$, $Zn(OSO_2C_4F_9)_2$, $Zn(OSO_2C_6H_4CH_3)_2$ (zinc p-toluenesulfonate), $Zn(OSO_2C_6H_5)_2$, $Zn(BF_4)_2$, $Zn(PF_6)_2$, $Hf(OTf)_4$ (hafnium trifluoromethanesulfonate), $Sn(OTf)_2$, $Al(OTf)_3$, and $Cu(OTf)_2$.

These catalysts can be used singly or in a combination of two or more.

The amount of the catalyst is in the range of, for example, 0.000001 to 0.1 mol, or preferably 0.00005 to 0.05 mol, per 1 mol of the amine. Even if the amount of the catalyst is more than the above range, no further remarkable reaction enhancing effect is observed, and at the same time, cost may increase due to an increase in the amount. On the other hand, when the amount is less than the above range, the reaction enhancing effect may not be obtained.

The method for adding the catalyst is not particularly limited, and the catalyst can be added by any of package addition, continuous addition, and intermittent addition in portions, which does not affect the reaction activity.

Then, this reaction may be carried out, for example, by charging a reaction vessel with the amine, urea (and as necessary N-unsubstituted carbamic acid ester), alcohol, and as necessary, a catalyst and a reaction solvent, under the above-described conditions, and stirring or mixing the mixture. For example, carbamate represented by the general formula (6) below is produced as a main product.

$$(R^2OCONH)n\text{-}R^1 \qquad (6)$$

(where $R^1$ is as defined for $R^1$ in the above-described formula (3), $R^2$ is as defined for $R^2$ in the above-described formula (4), and n is as defined for n in the above-described formula (3).)

Also, in this reaction, a gas containing alcohol (excess raw material alcohol), ammonia, and carbon dioxide is by-produced as a drained gas.

Further, in this reaction, when an N-unsubstituted carbamic acid ester is blended, alcohol represented, for example, by the following general formula (7) is by-produced:

$$R^2\text{—OH} \qquad (7)$$

(where $R^2$ is as defined for $R^2$ in the above formula (4).)

The by-produced alcohol is preferably the same type as that of the raw material alcohol (in the above-described formula (4)), and contained in the above-described gas along with the excess raw material alcohol.

Furthermore, in this reaction, sometimes N-unsubstituted carbamic acid ester, and carbonates (e.g., dialkylcarbonate, diarylcarbonate, alkylarylcarbonate, etc.) are also by-produced.

In this reaction, either of a batch reaction process or a continuous reaction process can be adopted.

Then, in this method, the above-described gas (drained gas containing alcohol, ammonia, and carbon dioxide) is absorbed with water to produce a gas absorption water, and at the same time, ammonia is separated (ammonia separation step) from the gas absorption water.

For the production of the gas absorption water, for example, water is allowed to contact the above-described gas by-produced in the carbamate-forming step under normal temperature and pressure.

The water is not particularly limited, and any water such as pure water, and ion-exchange water can be used. Preferably, the above-described by-produced (drained) water in the urea production step is used (water reusing step).

Furthermore, although to be described later, for the water, preferably, water remained at the time when alcohol is separated from the aqueous alcohol solution (described later) is used.

The amounts of the gas and water are not particularly limited, and for example, the amount of water relative to 1 $m^3$ of gas is, 0.00002 to 0.02 $m^3$, preferably 0.00004 to 0.01 $m^3$.

In the ammonia separation step, preferably, the above-described gas is absorbed with water in the presence of carbonate.

Carbonates are compounds containing carbonate ions ($CO_3^{2-}$) and are not particularly limited. Examples of the carbonate include inorganic carbonate, and organic carbonate.

Examples of the inorganic carbonate include carbonates of alkaline metal (e.g., lithium carbonate, sodium carbonate, potassium carbonate, etc.), carbonates of alkaline earth metal (e.g., magnesium carbonate, calcium carbonate, etc.), and carbonates of transition metal (e.g. copper carbonate, iron carbonate, silver carbonate, etc.).

Examples of the organic carbonate include amine salts such as alkanol amine salt.

Examples of alkanol amine salt include carbonate of monoethanolamine, carbonate of diethanolamine, carbonate of triethanolamine, carbonate of N-methylethanolamine, carbonate of N-methyldiethanolamine, carbonate of N-ethyldiethanolamine, carbonate of N,N-dimethylethanolamine, carbonate of N,N-diethylethanolamine, carbonate of 2-amino-2-methyl-1-propanol, and carbonate of diisopropanolamine.

These carbonates may be used singly or in a combination of two or more.

For the carbonate, preferably, inorganic carbonate, more preferably, carbonate of alkaline metal is used.

When an inorganic carbonate is used as the carbonate, for example, the above-described inorganic carbonate can be used as is, and furthermore, a compound that becomes inorganic carbonate by reaction with the above-described gas (drained gas containing alcohol, ammonia, and carbon dioxide) can also be used. Examples of such a compound include inorganic hydroxides (e.g., hydroxides of alkaline metal (e.g., lithium hydroxide, sodium hydroxide, potassium hydroxide, etc.), and hydroxides of alkaline earth metal (e.g., magnesium hydroxide, calcium hydroxide, etc.), etc.).

When the inorganic hydroxide is used, for example, carbonate (inorganic carbonate) can be obtained by reaction between the inorganic hydroxide and carbon dioxide contained in the above-described gas, and the carbonate can be reused, as described later in each of the steps. In such a case, the inorganic hydroxide is allowed to react with the above-described gas (carbon dioxide), and therefore the contact conditions for them are suitably set.

The gas absorption water is produced in this manner as an aqueous solution containing alcohol, ammonia, and carbon dioxide (preferably, also carbonate).

Furthermore, in this method, in the above-described gas, ammonia is separated as a component that remains without being absorbed in water.

The separated ammonia is used as a raw material component, preferably, in the above-described urea production step (ammonia reusing step).

Then, in this method, from the above-described gas absorption water, the aqueous alcohol solution is separated (aqueous alcohol solution separation step).

The method for separating the aqueous alcohol solution is not particularly limited, and for example, known separation apparatuses such as distillation column, and extraction column may be used.

Then, in this method, in the gas absorption water in which the aqueous alcohol solution is separated, preferably in the presence of carbonate, carbon dioxide gas is separated from the aqueous ammonia solution (ammonia/carbon dioxide separation step).

In the presence of carbonate, carbon dioxide gas can be separated efficiently from the aqueous ammonia solution.

The method for separating carbon dioxide gas from the aqueous ammonia solution in the gas absorption water is not particularly limited, and for example, known separation apparatuses such as distillation column and extraction column may be used.

At that time, carbonate is separated from carbon dioxide gas along with the aqueous ammonia solution.

Then, in this method, the aqueous ammonia solution (preferably, containing carbonate) separated in the ammonia/carbon dioxide separation step is mixed with water, and used for production of the gas absorption water in the above-described ammonia separation step (aqueous ammonia solution reusing step).

That is, in this method, to the water that absorbs the above-described by-produced gas (drained gas containing alcohol, ammonia, and carbon dioxide) in the production of carbamate, the aqueous ammonia solution is mixed. Then, the water (containing aqueous ammonia solution) is used for production of the gas absorption water.

With such a method, the water that produces gas absorption water contains ammonia before contacting gas, and therefore the amount of ammonia absorption with the water can be reduced, and of the ammonia contained in the gas, the proportion of the ammonia remained without being absorbed with water can be increased.

Thus, with such a method, ammonia can be separated from gas efficiently, and can be effectively used in the urea production step as a raw material component.

Furthermore, in this method, preferably, along with the aqueous ammonia solution, carbonate is used in the ammonia separation step (production of gas absorption water). That is in this method, carbonate is, after going through the ammonia separation step, the aqueous alcohol solution separation step, the ammonia/carbon dioxide separation step, and the aqueous ammonia solution reusing step sequentially, reused in the ammonia separation step, and repeatedly used in these steps.

Thus, with such a method, the carbonate once introduced can be circulated, and therefore continuous supply of carbonate is not necessary, and as a result, costs reduction can be achieved.

Furthermore, in this method, the aqueous ammonia solution can be allowed to directly contact the gas along with water, without mixing with water, to be used in production of the gas absorption water.

On the other hand, in this method, the carbon dioxide gas separated in the ammonia/carbon dioxide separation step can be released, and it is also possible to recover the separated carbon dioxide gas for use as a production raw material of urea (carbon dioxide gas reusing step) in the above-described urea production step.

With such a method, the carbon dioxide gas contained in the drained gas is reused in the urea production step, and therefore by-products of carbamate-forming reaction can be efficiently recovered and used effectively.

Furthermore, in this method, preferably, alcohol is separated from the aqueous alcohol solution separated as described above, and the alcohol is used in the above-described carbamate-forming step (alcohol reusing step).

The method for separating the alcohol from the aqueous alcohol solution is not particularly limited, and for example, known separation apparatuses such as distillation column and extraction column may be used.

The water obtained by separating alcohol from the aqueous alcohol solution is, preferably, reused in the ammonia separation step as water for producing the gas absorption water.

On the other hand, in this method, from the reaction solution obtained in the above-described carbamate-forming step, carbamate (the above-described formula (6)) is separated by a known method, and as necessary, for example, excessive (unreacted) urea (and as necessary N-unsubstituted carbamic acid ester), and depending on the case, by-produced N-unsubstituted carbamic acid ester, carbonate, etc. are separated as low-boiling components (light-boiling fractions).

With such a method for producing carbamate, a gas containing alcohol, ammonia, and carbon dioxide obtained from carbamate-forming reaction is absorbed with water, and therefore alkaline carbonate does not generate in the gas absorption water. Thus, ammonia in the gas absorption water can be recovered and reused.

Thus, with such a method for producing carbamate, by-products of carbamate-forming reaction can be efficiently recovered, and used effectively, and furthermore, waste components can be reduced; therefore, the method is advantageous in view of costs.

Furthermore, by absorbing a gas containing alcohol, ammonia, and carbon dioxide obtained from carbamate-forming reaction with water in the presence of carbonate, and separating carbon dioxide gas from the aqueous ammonia solution in the gas absorption water in the presence of carbonate, the aqueous ammonia solution can be recovered more efficiently and reused.

Thus, with such a method for producing carbamate, by-products of carbamate-forming reaction can be recovered more efficiently and effectively used.

Furthermore, with a method for producing carbamate of the present invention, after separating carbon dioxide gas from an aqueous ammonia solution in the presence of carbonate, the carbonate can be recovered and reused; therefore, the method is more advantageous in view of costs.

In the description given above, after separating the aqueous alcohol solution from the gas absorption water in the aqueous alcohol solution separation step, in the ammonia/carbon dioxide separation step, carbon dioxide gas is separated, in the gas absorption water from which the aqueous alcohol solution is separated, from the aqueous ammonia solution; however, the treatment method of the gas absorption water is not limited thereto, and for example, after separating the aqueous alcohol solution from the gas absorption water in the aqueous alcohol solution separation step, the aqueous ammonium carbonate solution obtained by separating the aqueous alcohol solution can be used in the above-described urea production step (ammonium carbonate reusing step).

That is, the gas absorption water from which the aqueous alcohol solution is separated contains ammonia and carbon dioxide, but these are usually in an equilibrium state with ammonium carbonate (ref: formula (8) below).

[Chemical Formula 1]

$$(NH_4)_2CO_3 \rightleftharpoons 2NH_3 + CO_2 + H_2O \tag{8}$$

Thus, by suitably adjusting production conditions for gas absorption water, and separation conditions for the aqueous alcohol solution, an aqueous ammonium carbonate solution can be obtained as a gas absorption water from which the aqueous alcohol solution is separated.

In such a case, the obtained aqueous ammonium carbonate solution can be used as a raw material component (that is, ammonia and carbon dioxide) in the above-described urea production step.

Furthermore, the present invention includes a method for producing isocyanate: in the method, the carbamate obtained by the above-described method for producing carbamate is thermally decomposed to produce isocyanate.

In the method for producing isocyanate of the present invention, carbamate is produced by the above-described method for producing carbamate (carbamate production step): and thereafter, isocyanate is produced by thermally decomposing the obtained carbamate (isocyanate production step).

To be more specific, in the method for producing isocyanate, carbamate obtained by the above-described method for producing carbamate is thermally decomposed to produce isocyanate represented by the general formula (9) below, the isocyanate corresponding to the above-described amine, and

$$R^1—(NCO)n \tag{9}$$

(where $R^1$ is as defined for $R^1$ in the above-described formula (3), and n is as defined for n in the above-described formula (3).)

alcohol represented by the general formula (10) below, which is a by-product.

$$R^2—OH \tag{10}$$

(where $R^2$ is as defined for $R^2$ in the above formula (4).)

There is no particular limitation on the thermal decomposition. Any known decomposition method such as a liquid phase method or a vapor phase method can be used.

In the vapor phase method, the isocyanate and alcohol produced by the thermal decomposition can be separated from a gaseous product mixture by fractional condensation. In the liquid phase method, the isocyanate and alcohol produced by the thermal decomposition can be separated, for example, by distillation or using a solvent and/or inert gas as a support substance.

As the thermal decomposition, a liquid phase method is preferable from the viewpoint of workability.

In such a method, carbamate is preferably thermally decomposed in the presence of an inert solvent.

The inert solvent is not particularly limited, as long as the inert solvent at least dissolves carbamate, is inactive to carbamate and isocyanate, and does not react at the time of thermal decomposition (that is, stable). To perform thermal decomposition reaction efficiently, the inert solvent has a boiling point that is higher than the isocyanate to be produced.

As such an inert solvent, aromatic hydrocarbons may be used.

Examples of the aromatic hydrocarbons include benzene (boiling point: 80° C.), toluene (boiling point: 111° C.), o-xylene (boiling point: 144° C.), m-xylene (boiling point: 139° C.), p-xylene (boiling point: 138° C.), ethylbenzene (boiling point: 136° C.), isopropylbenzene (boiling point: 152° C.), butylbenzene (boiling point: 185° C.), cyclohexylbenzene (boiling point: 237-340° C.), tetralin (boiling point: 208° C.), chlorobenzene (boiling point: 132° C.), o-dichlorobenzene (boiling point: 180° C.), 1-methylnaphthalene (boiling point: 245° C.), 2-methylnaphthalene (boiling point: 241° C.), 1-chloronaphthalene (boiling point: 263° C.), 2-chloronaphthalene (boiling point: 264-266° C.), triphenylmethane (boiling point: 358 to 359° C. (754 mmHg)), 1-phenylnaphthalene (boiling point: 324-325° C.), 2-phenylnaphthalene (boiling point: 357-358° C.), and biphenyl (boiling point: 255° C.).

These solvents are also available as commercially available products and examples thereof include Barrel Process Oil B-01 (aromatic hydrocarbon, boiling point: 176° C.), Barrel Process Oil B-03 (aromatic hydrocarbon, boiling point: 280° C.), Barrel Process Oil B-04AB (aromatic hydrocarbon, boiling point: 294° C.), Barrel Process Oil B-05 (aromatic hydrocarbon, boiling point: 302° C.), Barrel Process Oil B-27 (aromatic hydrocarbon, boiling point: 380° C.), Barrel Process Oil B-28AN (aromatic hydrocarbon, boiling point: 430° C.), Barrel Process Oil B-30 (aromatic hydrocarbon, boiling point: 380° C.), Barrel Therm 200 (aromatic hydrocarbon, boiling point: 382° C.). Barrel Therm 300 (aromatic hydrocarbon, boiling point: 344° C.), Barrel Therm 400 (aromatic hydrocarbon, boiling point: 390° C.), Barrel Therm 1H (aromatic hydrocarbon, boiling point: 215° C.), Barrel Therm 2H (aromatic hydrocarbon, boiling point: 294° C.), Barrel Therm 350 (aromatic hydrocarbon, boiling point: 302° C.), Barrel Therm 470 (aromatic hydrocarbon, boiling point: 310° C.), Barrel Therm PA (aromatic hydrocarbon, boiling point: 176° C.), Barrel Therm 330 (aromatic hydrocarbon, boiling point: 257° C.), and Barrel Therm 430 (aromatic hydrocarbon, boiling point: 291° C.) (hereinabove manufactured by Matsumura Oil Co., Ltd.); and NeoSK-OIL 1400 (aromatic hydrocarbon, boiling point: 391° C.), NeoSK-OIL 1300 (aromatic hydrocarbon, boiling point: 291° C.), NeoSK-OIL 330 (aromatic hydrocarbon, boiling point: 331° C.), NeoSK-OIL 170 (aromatic hydrocarbon, boiling point: 176° C.), NeoSK-OIL 240 (aromatic hydrocarbon, boiling point: 244° C.), KSK-OIL 260 (aromatic hydrocarbon, boiling point: 266° C.), and KSK-OIL 280 (aromatic hydrocarbon, boiling point: 303° C.) (hereinabove, manufactured by Soken Tecnix Co., Ltd.).

Furthermore, examples of the inert solvent include esters (e.g., dioctyl phthalate, didecyl phthalate, and didodecyl phthalate) and aliphatic hydrocarbons which are commonly used as a heat transfer medium.

These inert solvents can be used singly or in a combination of two or more.

The amount of the inert solvent relative to 1 part by mass of carbamate is in the range of 0.001 to 100 parts by mass, preferably 0.01 to 80 parts by mass, more preferably 0.1 to 50 parts by mass.

In the thermal decomposition, for example, the inert solvent is blended with carbamate, and after the carbamate is thermally decomposed, the inert solvent is separated, recovered, and blended again with the carbamate in thermal decomposition.

Thermal decomposition reaction of carbamate in the liquid phase method is reversible, and therefore preferably, to suppress the reaction opposite to the thermal decomposition reaction (that is, urethane-forming reaction between isocyanate represented by the above-described formula (9) and alcohol represented by the above-described formula (10)), in addition to thermally decomposing carbamate, isocyanate represented by the above-described formula (9) and/or alcohol represented by the above-described formula (10) are removed by a known method from the reaction mixture (decomposition solution), and they are separated.

Reaction conditions for the thermal decomposition reaction are, for example, as follows: preferably, the conditions are such that carbamate is thermally decomposed excellently, and at the same time, the isocyanate (the above-described formula (9)) and alcohol (the above-described formula (10)) produced in the thermal decomposition are evaporated, thus avoiding equilibrium state between carbamate and isocyanate, and further, side reactions such as polymerization of isocyanate is suppressed.

As the reaction conditions, more specifically, the thermal decomposition temperature is usually 350° C. or lower, preferably from 80 to 350° C., or more preferably from 100 to 300° C. At the thermal decomposition temperature lower than 80° C., a practical reaction rate may not be obtained. On the other hand, at the thermal decomposition temperature higher than 350° C., an undesired side reaction such as polymerization of isocyanates may occur. It is preferable that the pressure during the thermal decomposition reaction is a pressure for allowing the alcohol produced to be vaporized at the thermal decomposition reaction temperature specified above. For practical use, the pressure is preferably in the range of 0.133 to 90 kPa in terms of equipment and utilities.

In this method, a catalyst may be added as necessary.

The catalyst may be added, although the timing may be different depending on its types, at any of the following: at the time of above-described reaction, before and/or after distillation separation after the reaction, and before and/or after the separation of carbamate.

As the catalyst used for the thermal decomposition, at least one metal selected from the group consisting of Sn, Sb, Fe, Co, Ni, Cu, Cr, Ti, Pb, Mo, and Mn, or a compound thereof such as oxide, halide, carboxylate, phosphate, and organometallic compound, used for the urethane-forming reaction of an isocyanate and a hydroxyl group is used. Of these, Fe, Sn, Co, Sb, and Mn are preferably used in the thermal decomposition because they exhibit the effect of suppressing the production of by-products.

Examples of the metallic catalyst of Sn include tin oxide, tin chloride, tin bromide, tin iodide, tin formate, tin acetate, tin oxalate, tin octylate, tin stearate, tin oleate, tin phosphorate, dibutyltin dichloride, dibutyltin dilaurate, and 1,1,3,3-tetrabutyl-1,3-dilauryloxydistannoxane.

Examples of the metallic catalysts of Fe, Co, Sb, and Mn include acetate, benzoate, naphthenate, and acetylacetonate thereof.

The amount of the catalyst is in the range of 0.0001 to 5 mass %, or preferably 0.001 to 1 mass %, per the reaction solution, as a metal or a compound thereof.

The thermal decomposition reaction can be carried out by a batch reaction process in which the carbamate, the catalyst, and the inert solvent are added by a batch, or by a continuous reaction process in which the carbamate is added into the inert solvent containing the catalyst under reduced pressure.

In the thermal decomposition, isocyanate and alcohol are produced, and for example, allophanate, amines, urea, carbonate, carbamates, and carbon dioxide may also be produced by a side reaction in some cases. Therefore, as necessary, the isocyanate thus produced is purified by a known method.

The alcohol (the above formula (10)) obtained by the thermal decomposition is separated and recovered, and thereafter preferably used as a raw material component for the carbamate-forming reaction.

With such a method for producing isocyanate, industrially useful isocyanate as a raw material of polyurethane can be produced at low costs and efficiently.

In such a method, by removing isocyanate and alcohol from the decomposition solution obtained from thermal decomposition of carbamate, and as necessary, separating the solvent, isocyanate residue is obtained. The separated solvent can be used again for thermal decomposition.

That is, for example, when isocyanate is produced by producing carbamate by reaction between amine, urea (and as necessary N-unsubstituted carbamic acid ester), and alcohol, and thermally decomposing the carbamate, for example, the obtained carbamate, isocyanate, or intermediates thereof may cause unpreferable polymerization reaction such as multimerization, biuretization, or allophanatization in some cases. In such a case, by-products such as urea derivatives (biuret derivatives) or carbamate derivatives (allophanate derivatives) are obtained as isocyanate residues. The isocyanate residues may contain, for example, unreacted urea or carbamate in some cases.

These isocyanate residues are recovered as necessary, and for example, recycled and/or disposed of by a known method.

FIG. 1 is a schematic diagram illustrating the configuration of a first embodiment of a plant as a carbamate production system and an isocyanate production system in which a method for producing carbamate and a method for producing isocyanate of the present invention are used.

In the following, with reference to FIG. 1, the first embodiment of a plant in which the above-described method for producing carbamate and method for producing isocyanate are industrially performed, is described.

In FIG. 1, the plant 1 is an isocyanate production system in which the above-described method for producing isocyanate is used, and includes a carbamate production system 2 in which the above-described method for producing carbamate is used, and a thermal decomposition apparatus 3 in which isocyanate is produced by thermally decomposing the carbamate obtained in the carbamate production system 2.

The carbamate production system 2 includes a urea production apparatus 4, a carbamate-forming reaction apparatus 5, an ammonia separation apparatus 6, an aqueous alcohol solution separation apparatus 7, an ammonia/carbon dioxide separation apparatus 40, an aqueous ammonia solution reusing apparatus 41, a carbon dioxide gas reusing system 42, an ammonia reusing apparatus 9, an alcohol reusing apparatus 10, and a water reusing system 11.

In the plant 1, the urea production apparatus 4 is provided to produce urea by the above-described urea production step.

The urea production apparatus 4 includes a urea production tank 12, a carbon dioxide feed pipe 13, an ammonia feed pipe 14, and a urea transporting pipe 15 that are connected to the urea production tank 12.

The urea production tank 12 is a known reaction tank for producing urea by reaction between carbon dioxide and ammonia, and is composed of a heat-resistant and pressure-resistant vessel whose temperature and pressure can be controlled.

To the urea production tank 12, the downstream end of a carbon dioxide gas transporting pipe 46 (described later) of a carbon dioxide gas reusing system 42 is connected.

Although not shown, the urea production tank 12 may be provided with, for example, an inert gas feed pipe for substituting the inside of the urea production tank 12 with inert gas (i.e., nitrogen gas), and a stirrer for stirring within the urea production tank 12, as necessary.

The carbon dioxide feed pipe 13 is a carbon dioxide feed line for feeding carbon dioxide to the urea production tank 12, and its downstream end is connected to the urea production tank 12. Although not shown, the upstream end thereof is connected to a carbon dioxide inlet line for introducing carbon dioxide.

The ammonia feed pipe 14 is an ammonia feed line for feeding ammonia to the urea production tank 12, and its downstream end is connected to the urea production tank 12. Although not shown, the upstream end thereof is connected to an ammonia inlet line for introducing ammonia.

The downstream end of an ammonia reflux pipe 26, which will be described later, of the ammonia reusing apparatus 9 is connected to the ammonia feed pipe 14 at a position along the flow direction thereof.

The urea transporting pipe 15 is a urea transporting line for transporting the urea produced in the urea production tank 12 to the reaction tank 16 (described later), and its upstream end is connected to the urea production tank 12, and its downstream end is connected to a reaction tank 16 (described later).

The carbamate-forming reaction apparatus 5 is provided in the plant 1 in order to produce a reaction solution containing carbamate by reaction between amine, urea (and as necessary N-unsubstituted carbamic acid ester), and alcohol, and to by-produce a gas containing alcohol, ammonia, and carbon dioxide.

The carbamate-forming reaction apparatus 5 includes a reaction tank 16, and an amine feed pipe 17 and an alcohol feed pipe 19 that are connected to the reaction tank 16.

The reaction tank 16 is a known carbamate-forming reaction tank for producing carbamate by carbamate-forming reaction between amine, urea (and as necessary N-unsubstituted carbamic acid ester), and alcohol, and is composed of a heat-resistant and pressure-resistant vessel whose temperature and pressure can be controlled.

To the reaction tank 16, the downstream end of a urea transporting pipe 15 of the urea production apparatus 4 is connected.

Although not shown, the reaction tank 16 may be provided with, for example, a catalyst feed pipe for feeding a catalyst to the reaction tank 16, an inert gas feed pipe for substituting the inside of the reaction tank 16 with inert gas (i.e., nitrogen gas), and a stirrer for stirring within the reaction tank 16, as necessary.

The amine feed pipe 17 is an amine feed line for feeding amine to the reaction tank 16, and its downstream end is connected to the reaction tank 16. Although not shown, the upstream end thereof is connected to an amine inlet line for introducing amine.

The alcohol feed pipe 19 is an alcohol feed line for feeding alcohol to the reaction tank 16, and its downstream end is connected to the reaction tank 16. Although not shown, the upstream end thereof is connected to an alcohol inlet line for introducing alcohol.

The downstream end of a first alcohol reflux pipe 29 (described later), and the downstream end of a second alcohol reflux pipe 35 (described later) are connected to the alcohol feed pipe 19 at a position along the flow direction thereof.

The carbamate-forming reaction apparatus 5 may also be provided with, for example, a urea feed pipe 18 and an N-unsubstituted carbamic acid ester feed pipe 37, as necessary (ref: broken line in FIG. 1).

The urea feed pipe 18 is a urea feed line for feeding urea to the reaction tank 16, and its downstream end is connected at a position along the flow direction of the urea transporting pipe 15 of the urea production apparatus 4. Although not shown, the upstream end thereof is connected to a urea inlet line for introducing urea.

The N-unsubstituted carbamic acid ester feed pipe 37 is an N-unsubstituted carbamic acid ester feed line for feeding, as necessary, N-unsubstituted carbamic acid ester to the reaction tank 16, and its downstream end is connected to the reaction tank 16. Although not shown, the upstream end thereof is connected to an N-unsubstituted carbamic acid ester inlet line for introducing N-unsubstituted carbamic acid ester.

The ammonia separation apparatus 6 is provided in the plant 1 in order to absorb the gas by-produced in the reaction tank 16, preferably, in the presence of carbonate, with water, to produce a gas absorption water (aqueous solution containing alcohol, ammonia, and carbon dioxide (preferably, also carbonate)), and to separate ammonia.

The ammonia separation apparatus 6 includes an absorption tank 20, and a gas transporting pipe 21 and a water feed pipe 22 that are connected to the absorption tank 20.

The absorption tank 20 is a known absorption tank for absorbing the gas by-produced at the reaction tank 16 with water, and for producing a gas absorption water; and is composed of a heat-resistant and pressure-resistant vessel whose temperature and pressure can be controlled.

Although not shown, the absorption tank 20 may be provided with, for example, an inert gas feed pipe for substituting the inside the absorption tank 20 with inert gas (e.g., nitrogen gas, etc.), and a stirrer for stirring within the absorption tank 20, as necessary.

The gas transporting pipe 21 is a gas transporting line for transporting the gas by-produced in the reaction tank 16 to the absorption tank 20, and its downstream end is connected to the absorption tank 20. The upstream end thereof is connected to the reaction tank 16 in the carbamate-forming reaction apparatus 5.

The water feed pipe 22 is a water feed line for feeding water to the absorption tank 20, and its downstream end is connected to the absorption tank 20. Although not shown, the upstream end thereof is connected to a water inlet line for introducing water.

The downstream end of a water drain pipe 30 (described later), the downstream end of a water reflux pipe 36 (described later), and the downstream end of an aqueous ammonia solution transporting pipe 45 (described later) are connected to the water feed pipe 22 at a position along the flow direction thereof.

The aqueous alcohol solution separation apparatus 7 is provided in the plant 1 in order to separate an aqueous alcohol solution from the gas absorption water (aqueous solution containing alcohol, ammonia, carbon dioxide, and carbonate) obtained in the absorption tank 20.

The aqueous alcohol solution separation apparatus 7 includes a first separation column 23, and a first gas absorption water transporting pipe 24 connected to the first separation column 23.

The first separation column 23 is a separation column for separating the aqueous alcohol solution from the gas absorption water obtained in the ammonia separation apparatus 6, and is composed of a known separation column such as a distillation column, an extraction column, or a liquid separation column.

The first gas absorption water transporting pipe 24 is a first gas absorption water transporting line for transporting the gas absorption water obtained in the ammonia separation apparatus 6 to the first separation column 23, and its downstream end is connected to the first separation column 23. The upstream end thereof is connected to the absorption tank 20 in the ammonia separation apparatus 6.

The ammonia/carbon dioxide separation apparatus 40 is provided in the plant 1 in order to separate carbon dioxide gas from the aqueous ammonia solution, preferably, in the presence of carbonate, in the gas absorption water (containing ammonia and carbon dioxide (preferably, also carbonate)) from which the aqueous alcohol solution is separated in the aqueous alcohol solution separation apparatus 7.

The ammonia/carbon dioxide separation apparatus 40 includes a third separation column 43, and a second gas absorption water transporting pipe 44 connected to the third separation column 43.

The third separation column 43 is a separation column for separating aqueous ammonia solution and carbon dioxide gas from the gas absorption water (residue after separation of aqueous alcohol solution, and containing ammonia and carbon dioxide (preferably, also carbonate)) obtained in the aqueous alcohol solution separation apparatus 7, preferably, in the presence of carbonate, and is composed of a known separation column such as a distillation column or an extraction column.

The second gas absorption water transporting pipe 44 is a second gas absorption water transporting line for transporting the gas absorption water (residue after separation of aqueous alcohol solution, and containing ammonia and carbon dioxide (preferably, also carbonate)) obtained in the aqueous alcohol solution separation apparatus 7 to the third separation column 43, and its downstream end is connected to the third separation column 43. The upstream end thereof is connected to the first separation column 23 in the aqueous alcohol solution separation apparatus 7.

The aqueous ammonia solution reusing apparatus 41 is provided in the plant 1 in order to mix the aqueous ammonia solution separated in the ammonia/carbon dioxide separation apparatus 40 with water (water fed to the water feed pipe 22 of the ammonia separation apparatus 6), and to be used for production of gas absorption water in the absorption tank 20.

The aqueous ammonia solution reusing apparatus 41 includes an aqueous ammonia solution transporting pipe 45.

The aqueous ammonia solution transporting pipe 45 is an aqueous ammonia solution transporting line for transporting the aqueous ammonia solution (and carbonate) separated in the third separation column 43 to the ammonia separation apparatus 6 (water feed pipe 22), and its upstream end is connected to the third separation column 43 in the ammonia/carbon dioxide separation apparatus 40, and its downstream end is connected at a position along the flow direction of the water feed pipe 22.

Although not shown, in the plant 1, the downstream end of the aqueous ammonia solution transporting pipe 45 can also be connected directly to the absorption tank 20. In this fashion, the aqueous ammonia solution (and carbonate) is directly supplied to the absorption tank 20 without mixing with water in the water feed pipe 22, and allowed to contact directly with gas along with the water supplied from the water feed pipe 22, to be used for production of the gas absorption water.

The carbon dioxide gas reusing system 42 is provided in the plant 1 in order to recover carbon dioxide gas separated in the ammonia/carbon dioxide separation apparatus 40, to be used in the urea production apparatus 4.

The carbon dioxide gas reusing system 42 includes a carbon dioxide gas transporting pipe 46.

The carbon dioxide gas transporting pipe 46 is a carbon dioxide gas transporting line for transporting carbon dioxide gas separated in the third separation column 43 to the urea production tank 12, and the upstream end thereof is connected to the third separation column 43 in the ammonia/carbon dioxide separation apparatus 40, and the downstream end thereof is connected to the urea production tank 12.

The ammonia reusing apparatus 9 is provided in the plant 1 in order to use, in the urea production apparatus 4, the ammonia separated in the ammonia separation apparatus 6.

The ammonia reusing apparatus 9 includes an ammonia reflux pipe 26.

The ammonia reflux pipe 26 is an ammonia reflux line for refluxing ammonia separated in the absorption tank 20 to the ammonia feed pipe 14 in the urea production apparatus 4; and the upstream end thereof is connected to the absorption tank 20 in the ammonia separation apparatus 6, and the downstream end thereof is connected to the ammonia feed pipe 14 at a position along the flow direction of the ammonia feed pipe 14.

The alcohol reusing apparatus 10 is provided in the plant 1 in order to separate alcohol from the aqueous alcohol solution, and use the alcohol in the carbamate-forming reaction apparatus 5.

The alcohol reusing apparatus 10 includes a second separation column 27, and an aqueous alcohol solution transporting pipe 28 and a first alcohol reflux pipe 29 that are connected the second separation column 27.

The second separation column 27 is a separation column for separating alcohol from the aqueous alcohol solution separated in the aqueous alcohol solution separation apparatus 7, and is composed of a known separation column such as a distillation column, an extraction column, or a liquid separation column.

The aqueous alcohol solution transporting pipe 28 is an aqueous alcohol solution transporting line for transporting the aqueous alcohol solution separated in the aqueous alcohol solution separation apparatus 7 to the second separation column 27; and its downstream end is connected to the second separation column 27. The upstream end thereof is connected to the first separation column 23 in the aqueous alcohol solution separation apparatus 7.

The first alcohol reflux pipe 29 is a first alcohol reflux line for refluxing the alcohol separated in the second separation column 27 to the alcohol feed pipe 19 in the carbamate-forming reaction apparatus 5; and the upstream end thereof is connected to the second separation column 27, and the downstream end thereof is connected to the alcohol feed pipe 19 at a position along the flow direction of the alcohol feed pipe 19.

The alcohol reusing apparatus 10 further includes a water reflux pipe 36.

The water reflux pipe 36 is a water reflux line for refluxing the water obtained by separating alcohol from the aqueous alcohol solution in the second separation column 27 to the water feed pipe 22 in the ammonia separation apparatus 6; and the upstream end thereof is connected to the second separation column 27, and the downstream end thereof is connected to the water feed pipe 22 at a position along the flow direction of the water feed pipe 22.

The water reusing system 11 is provided in the plant 1 in order to use the water drained in the urea production apparatus 4 in the ammonia separation apparatus 6.

The water reusing system 11 includes a water drain pipe 30.

The water drain pipe 30 is a water drain line for draining the water obtained in the urea production tank 12, and transporting to the water feed pipe 22 in the ammonia separation apparatus 6; and the upstream end thereof is connected to the urea production tank 12 in the urea production apparatus 4, and the downstream end thereof is connected to the water feed pipe 22 at a position along the flow direction of the water feed pipe 22.

The thermal decomposition apparatus 3 is provided in the plant 1 in order to thermally decompose the reaction solution (to be more specific, a reaction solution containing carbamate obtained in the carbamate-forming reaction apparatus 5 in the above-described carbamate production system 2) into isocyanate and alcohol.

The thermal decomposition apparatus 3 includes a thermal decomposition tank 31, and a reaction solution transporting pipe 32, an isocyanate drain pipe 33, a residue drain pipe 34, and a second alcohol reflux pipe 35 that are connected to the thermal decomposition tank 31.

The thermal decomposition tank 31 is a known decomposition tank for heating the reaction solution obtained in the carbamate-forming reaction apparatus 5 to thermally decompose into isocyanate and alcohol; and is composed of a heat-resistant and pressure-resistant vessel whose temperature and pressure can be controlled.

The thermal decomposition tank 31 includes, although not shown, as necessary, for example, a solvent feed pipe for feeding a solvent to the thermal decomposition tank 31, a catalyst feed pipe for feeding a catalyst to the thermal decomposition tank 31, an inert gas feed pipe for substituting the inside the thermal decomposition tank 31 with inert gas (e.g., nitrogen gas, etc.), and a stirrer for stirring within the thermal decomposition tank 31.

The reaction solution transporting pipe 32 is a reaction solution transporting line for transporting the reaction solution to the thermal decomposition tank 31; and the downstream end thereof is connected to the thermal decomposition tank 31. The upstream end thereof is connected to the reaction tank 16 in the carbamate-forming reaction apparatus 5.

The isocyanate drain pipe 33 is an isocyanate drain line for draining, from the plant 1, the isocyanate obtained by thermal decomposition of the reaction solution, and the upstream end thereof is connected to the thermal decomposition tank 31. The downstream end thereof is connected to an isocyanate purifying line for purifying the isocyanate, although not shown.

The residue drain pipe 34 is a residue drain line for draining the residue (isocyanate residue) obtained at the time of decomposing the reaction solution into isocyanate and alcohol; and the upstream end thereof is connected to the thermal decomposition tank 31. The downstream end thereof is connected to a residue storage tank where the residue is stored, although not shown.

The second alcohol reflux pipe 35 is a second alcohol reflux line for refluxing the alcohol obtained by decomposing the reaction liquid in the thermal decomposition tank 31 to the alcohol feed pipe 19 in the carbamate-forming reaction apparatus 5; and the upstream end thereof is connected to the thermal decomposition tank 31, and the downstream end thereof is connected to the alcohol feed pipe 19 at a position along the flow direction of the alcohol feed pipe 19.

Next, description is given below of a method for producing carbamate, producing isocyanate by using the obtained carbamate, and also reusing the by-produced gas at the time of carbamate production, with the plant 1.

In this method, first, urea is produced in the urea production apparatus 4.

For production of the urea, the urea production apparatus 4 is continuously operated such that, carbon dioxide and ammonia, which are raw materials for urea, are pressure-transported from the carbon dioxide feed pipe 13 and the ammonia feed pipe 14, respectively, and continuously fed to the urea production tank 12.

The thus-obtained urea is fed to the urea transporting pipe 15, and to be described later, pressure-transported to the reaction tank 16.

Next, in this method, carbamate is produced in the carbamate-forming reaction apparatus 5.

In the production of carbamate, the carbamate-forming reaction apparatus 5 is continuously operated such that amine, urea, and alcohol, which are raw materials for the carbamate, are pressure-transported from the amine feed pipe 17, the urea transporting pipe 15, and the alcohol feed pipe 19, respectively, in the above-described amount, and continuously fed to the reaction tank 16. When the urea transported from the urea transporting pipe 15 is insufficient, as necessary, urea is supplied from the urea feed pipe 18 as a raw material component.

Furthermore, as necessary, as raw material component, N-unsubstituted carbamic acid ester is continuously fed from the N-unsubstituted carbamic acid ester feed pipe 37 (ref: broken line in FIG. 1), and furthermore, along with these raw material components, a catalyst is fed from a catalyst feed pipe (not shown).

Then, in this method, in the reaction tank 16, amine, urea (and as necessary N-unsubstituted carbamic acid ester), and alcohol undergo carbamate-forming reaction, and this produces a reaction solution containing carbamate, by-produced N-unsubstituted carbamic acid ester and carbonate. The thus obtained reaction solution is fed to the reaction solution transporting pipe 32, and pressure-transported to the thermal decomposition apparatus 3. The N-unsubstituted carbamic acid ester and carbonate contained in the reaction solution is distilled and recovered as light-boiling fractions as necessary, before transported to the thermal decomposition apparatus 3.

Meanwhile, in the reaction tank 16, a gas containing, as drained gas, alcohol (contains excess alcohol, and, by-produced alcohol in some case), ammonia, and carbon dioxide is by-produced.

The thus obtained gas is fed to the gas transporting pipe 2 and transported to the absorption tank 20.

Next, in this method, in the absorption tank 20 (ammonia separation apparatus 6), preferably, in the presence of carbonate, the gas is absorbed with water, thereby producing a gas absorption water, and at the same time separating ammonia.

In the production of the gas absorption water, and separation of ammonia, the ammonia separation apparatus 6 is continuously operated, and the above-described gas is transported from the gas transporting pipe 21, and at the same time, water is pressure-transported from the water feed pipe 22, and gas and water are continuously fed to the absorption tank 20.

At this time, when carbonate is used, at the time of initial operation of the plant 1, the absorption tank 20 is charged in advance with carbonate, or a compound (e.g., inorganic hydroxide, etc.) that reacts with gas to be carbonate. To be more specific, for example, the above-described compound is fed as an aqueous solution from the water feed pipe 22. When the plant 1 is to be continuously operated, as described later, carbonate (including carbonate obtained by reaction of inorganic hydroxide with gas) is circulated and fed to the absorption tank 20 by the aqueous ammonia solution reusing apparatus 41.

In this fashion, in the absorption tank 20, gas is allowed to contact water, preferably in the presence of carbonate; gas is absorbed in water; gas absorption water containing alcohol, ammonia, and carbon dioxide (preferably, also carbonate) is produced; and ammonia is separated as a component that remains without being absorbed in water in the gas.

The ammonia separated in the absorption tank 20 is transported to the ammonia reflux pipe 26 in the ammonia reusing apparatus 9, and continuously refluxed and fed to the ammonia feed pipe 14 of the urea production apparatus 4. In this manner, the ammonia separated from gas is used for urea production.

Next, in this method, in the aqueous alcohol solution separation apparatus 7, an aqueous alcohol solution is separated from the gas absorption water.

In this separation, the aqueous alcohol solution separation apparatus 7 is continuously operated, and the gas absorption water produced in the absorption tank 20 is pressure-transported to the first gas absorption water transporting pipe 24, to be continuously fed to the first separation column 23.

Then, in the first separation column 23, aqueous alcohol solution is separated from the gas absorption water, and, for example, drained from the top of the column.

Meanwhile, in the gas absorption water from which the aqueous alcohol solution is separated, in the ammonia/carbon dioxide separation apparatus 40, carbon dioxide gas is separated from the aqueous ammonia solution.

To be more specific, the gas absorption water obtained by separating the aqueous alcohol solution in the first separation column 23 is fed to the second gas absorption water transporting pipe 44 of the ammonia/carbon dioxide separation apparatus 40, and continuously fed to the third separation column 43.

Then, in the third separation column 43, the aqueous ammonia solution (and carbonate) is separated from the gas absorption water, and drained from the bottom of the column, and carbon dioxide gas is separated, and, for example, drained from the top of the column.

Next, in this method, in the aqueous ammonia solution reusing apparatus 41, the aqueous ammonia solution (and carbonate) is fed to the ammonia separation apparatus 6, and used for production of gas absorption water in the ammonia separation apparatus 6.

To be more specific, the aqueous ammonia solution separated in the third separation column 43 is fed to the aqueous ammonia solution transporting pipe 45 of the aqueous ammonia solution reusing apparatus 41, and fed to the water feed pipe 22 of the ammonia separation apparatus 6 from the aqueous ammonia solution transporting pipe 45, and continuously refluxed and fed to the absorption tank 20 of the ammonia separation apparatus 6 from the water feed pipe 22. At this time, the aqueous ammonia solution and carbonate are mixed with water fed from the water feed pipe 22, and used for the production of gas absorption water in the absorption tank 20.

Furthermore, in this method, carbon dioxide gas is recovered in the carbon dioxide gas reusing system 42, and the carbon dioxide gas is fed to the urea production apparatus 4, and used in the urea production apparatus 4.

To be more specific, carbon dioxide gas separated in the third separation column 43 is fed to the carbon dioxide gas transporting pipe 46 of the carbon dioxide gas reusing system 42, and continuously refluxed and fed to the urea production tank 12 of the urea production apparatus 4 from the carbon dioxide gas transporting pipe 46. In this fashion, carbon dioxide gas is used for the production of urea in the urea production apparatus 4.

Next, in this method, alcohol is separated from the aqueous alcohol solution in the alcohol reusing apparatus 10.

In this separation, the alcohol reusing apparatus 10 is continuously operated; the aqueous alcohol solution separated in the aqueous alcohol solution separation apparatus 7 is pressure-transported to the aqueous alcohol solution transporting pipe 28, and continuously fed to the second separation column 27.

Then, in the second separation column 27, alcohol is separated from the aqueous alcohol solution, and drained, for example, from the side portion of the column.

The drained alcohol is pressure-transported to the first alcohol reflux pipe 29, and continuously refluxed and fed to the alcohol feed pipe 19 of the carbamate-forming reaction apparatus 5. In this fashion, alcohol is used in the carbamate-forming reaction apparatus 5.

Meanwhile, water obtained by separating alcohol from the aqueous alcohol solution is drained, for example, from the top of the column; pressure-transported to the water reflux pipe 36; and continuously refluxed and fed to the water feed pipe 22 of the ammonia separation apparatus 6 from the water reflux pipe 36. In this fashion, water is used in the ammonia separation apparatus 6.

Next, in this method, in the thermal decomposition apparatus 3, the reaction solution (reaction solution obtained by carbamate-forming reaction in the reaction tank 16) is thermally decomposed.

In this thermal decomposition of the reaction solution, the thermal decomposition apparatus 3 is continuously operated, and the reaction solution fed through the reaction solution transporting pipe 32 is heated and thermally decomposed in the thermal decomposition tank 31 under the above-described conditions.

In this fashion, isocyanate and alcohol are obtained as a decomposition solution, and along with isocyanate and alcohol, isocyanate residue is obtained.

The isocyanate obtained in the thermal decomposition tank 31 is drained through the isocyanate drain pipe 33, and transported to an isocyanate purifying line, which is not shown.

Meanwhile, the alcohol obtained in the thermal decomposition tank 31 is, after separated from the decomposition solution, introduced into the first alcohol reflux pipe 35, and refluxed to the alcohol feed pipe 19 from the first alcohol reflux pipe 35. In this fashion, alcohol is fed to the reaction tank 16.

Then, the isocyanate residue obtained in the thermal decomposition tank 31 is transported to the residue storage tank (not shown) through the residue drain pipe 34, and after temporarily stored in the residue storage tank (not shown), for example, recycled and/or disposed of.

In such a plant 1, a gas containing alcohol, ammonia, and carbon dioxide obtained from carbamate-forming reaction is absorbed with water, and therefore alkaline carbonate does not generate in the gas absorption water, and thus ammonia in the gas absorption water can be recovered and reused.

To be more specific, with such a plant 1, the aqueous ammonia solution contained in the gas absorption water is mixed with the water used for production of gas absorption water, and therefore the ammonia concentration before the water makes contact with the gas can be increased. As a result, the ammonia absorption amount of water can be decreased, and of the ammonia contained in the gas, the proportion of the ammonia remained without being absorbed with water can be increased. Thus, with such a plant 1, ammonia can be separated from gas, and can be effectively used as a raw material component in the urea production apparatus 4.

Furthermore, the gas obtained by the carbamate-forming reaction is absorbed with water in the presence of carbonate, and by separating carbon dioxide gas from the aqueous ammonia solution in the presence of carbonate in the obtained gas absorption water, the aqueous ammonia solution can be recovered and reused more efficiently.

Also, when carbonate is used in the plant 1, in this method, carbonate is reused in the ammonia separation apparatus 6, after sequentially passing through the ammonia separation apparatus 6, the aqueous alcohol solution separation apparatus 7, the ammonia/carbon dioxide separation apparatus 40, and the aqueous ammonia solution reusing apparatus 41, and repeatedly used in these systems.

Thus, with such a plant 1, the carbonate once introduced can be circulated, and therefore continuous supply of carbonate is not necessary, and as a result, costs reduction can be achieved.

Furthermore, with such a plant 1, carbon dioxide contained in the gas can be reused in the urea production apparatus 4. Therefore, by-products of carbamate-forming reaction can be efficiently recovered, and used effectively.

Furthermore, with such a plant 1, the ammonia contained in the by-produced gas in the carbamate-forming reaction and remained without being absorbed in water is separated in the ammonia separation apparatus 6, and reused in the urea production apparatus 4.

Furthermore, with such a plant 1, the alcohol contained in the aqueous alcohol solution after separating the aqueous alcohol solution from the gas absorption water is separated in the alcohol reusing apparatus 10, and can be reused in the carbamate-forming reaction apparatus 5.

Furthermore, with such a plant 1, water drained from the urea production apparatus 4 can be reused as the water for absorbing gas in the ammonia separation apparatus 6 by the water reusing system 11.

Furthermore, with such a plant 1, the water obtained by separating alcohol from the aqueous alcohol solution in the alcohol reusing apparatus 10 can be reused as a water for absorbing gas in the ammonia separation apparatus 6.

Furthermore, with such a plant 1, the alcohol obtained by thermally decomposing the reaction solution in the thermal decomposition apparatus 3 can be reused in the carbamate-forming reaction apparatus 5.

Thus, with such a plant 1, by-products of carbamate-forming reaction can be efficiently recovered, and used effectively, and furthermore, waste components can be reduced; therefore it is advantageous in view of costs.

Furthermore, with such a plant 1, isocyanate, which is industrially useful as a raw material of polyurethane can be produced at low costs and efficiently.

Also, with such a plant 1, after separating carbon dioxide gas from the aqueous ammonia solution in the presence of carbonate, the carbonate can be recovered and reused; therefore, it is advantageous in view of costs.

Furthermore, with such a plant 1, isocyanate, which is industrially useful as a raw material of polyurethane, can be produced at low costs and efficiently.

Figure 2:
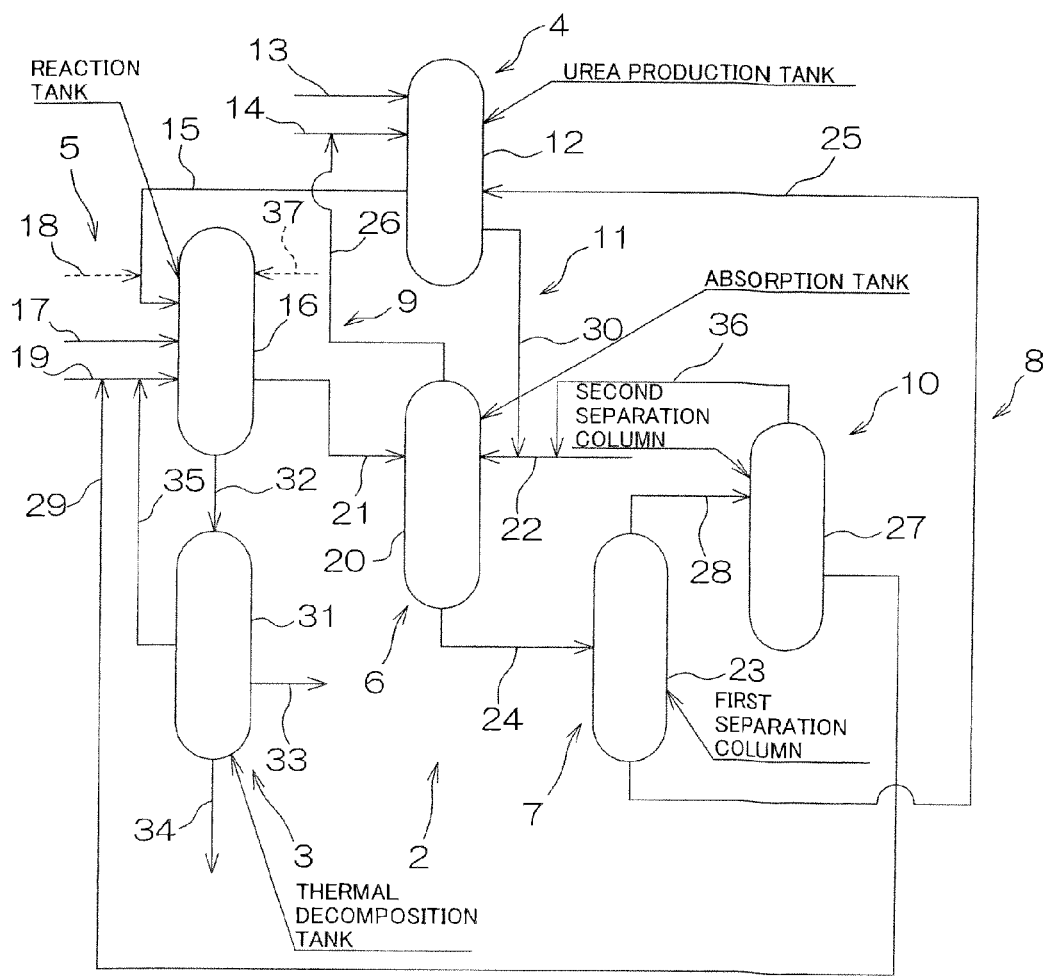
FIG. 2 is a schematic diagram illustrating the configuration of a second embodiment of a plant as a carbamate production system and an isocyanate production system in which a method for producing carbamate and a method for producing isocyanate of the present invention are used.

FIG. 2 is a schematic diagram illustration, the configuration of a second embodiment of a plant as a carbamate production system and an isocyanate production system in which a method for producing carbamate and a method for producing isocyanate of the present invention are used.

In the following, with reference to FIG. 2, the second embodiment of a plant in which the above-described method for producing carbamate and method for producing isocyanate are industrially performed, is described. Those systems and apparatuses corresponding to the above-described systems and apparatuses are designated with the same reference numerals in FIG. 2, and detailed descriptions thereof are omitted.

In the description above, the carbamate production system 2 includes the urea production apparatus 4, the carbamate-forming reaction apparatus 5, the ammonia separation apparatus 6, the aqueous alcohol solution separation apparatus 7, the ammonia/carbon dioxide separation apparatus 40, the aqueous ammonia solution reusing apparatus 41, the carbon dioxide gas reusing system 42, the ammonia reusing apparatus 9, the alcohol reusing apparatus 10, and the water reusing system 11; however, for example, instead of the ammonia/carbon dioxide separation apparatus 40, the aqueous ammonia solution reusing apparatus 41, and the carbon dioxide gas reusing system 42, an ammonium carbonate reusing apparatus 8 can be included.

The ammonium carbonate reusing apparatus 8 is provided in the plant 1 in order to use, in the urea production apparatus 4, the aqueous ammonium carbonate solution obtained by separating the aqueous alcohol solution from the gas absorption water.

The ammonium carbonate reusing apparatus 8 includes an aqueous ammonium carbonate solution transporting pipe 25.

The aqueous ammonium carbonate solution transporting pipe 25 is an aqueous ammonium carbonate solution transporting line for transporting the aqueous ammonium carbonate solution separated in the first separation column 23 to the urea production tank 12, and the upstream end thereof is connected to the first separation column 23 in the aqueous alcohol solution separation apparatus 7, and downstream end thereof is connected to the urea production tank 12.

Next, description is given below of a method for production of carbamate, production of isocyanate using the obtained carbamate with the plant 1, and reuse of the gas by-produced at the time of carbamate production.

In this method, in the same manner as described above, first, urea is produced in the urea production apparatus 4, and then carbamate is produced in the carbamate-forming reaction apparatus 5.

Next, in this method, in the same manner as described above, in the absorption tank 20 (ammonia separation apparatus 6), gas is absorbed with water, and gas absorption water is produced, and at the same time, ammonia is separated, and then in the aqueous alcohol solution separation apparatus 7, the aqueous alcohol solution is separated from the gas absorption water. At this time, the residual gas absorption water from which the aqueous alcohol solution is separated contains an aqueous ammonium carbonate solution.

Thereafter, in this method, in the ammonium carbonate reusing apparatus 8, the aqueous ammonium carbonate solution obtained by separating the aqueous alcohol solution from the gas absorption water is fed to the urea production apparatus 4, and used in the urea production apparatus 4.

That is, in the gas absorption water from which the aqueous alcohol solution is separated, ammonia and carbon dioxide are contained, but these are usually in equilibrium state with the ammonium carbonate (ref the above-described formula (8)).

Thus, by suitably adjusting, for example, production conditions for gas absorption water, and separation conditions for the aqueous alcohol solution, an aqueous ammonium carbonate solution can be obtained as a gas absorption water from which the aqueous alcohol solution is separated.

In such a case, the obtained aqueous ammonium carbonate solution can be used as a raw material component (that is, ammonia and carbon dioxide) in the urea production apparatus 4.

To be more specific, the aqueous ammonium carbonate solution obtained by separating the aqueous alcohol solution in the first separation column 23 is fed to the aqueous ammonium carbonate solution transporting pipe 25 in the ammonium carbonate reusing apparatus 8, and continuously refluxed and fed to the urea production tank 12 in the urea production apparatus 4 from the aqueous ammonium carbonate solution transporting pipe 25. In this fashion, the ammonium carbonate contained in the aqueous ammonium carbonate solution is used for the production of urea in the urea production apparatus 4. The water contained in the aqueous ammonium carbonate solution is drained from the urea production apparatus 4 through the water drain pipe 30 in the water reusing system 11, and transported to the water feed pipe 22. In this fashion, the water drained from the urea production apparatus 4 is reused in the ammonia separation apparatus 6.

Next, in this method, in the same manner as described above, in the alcohol reusing apparatus 10, alcohol is separated from the aqueous alcohol solution, and drained, for example, from the side portion of the column.

Thereafter, in this method, in the same manner as described above, in the thermal decomposition apparatus 3, reaction solution (reaction solution obtained by carbamate-forming reaction in the reaction tank 16) is thermally decomposed. In this fashion, isocyanate and alcohol are obtained as a decomposition solution, and isocyanate residue is obtained along with isocyanate and alcohol.

The isocyanate obtained in the same manner as described above is transported to an isocyanate purifying line, which is not shown, and the obtained alcohol is fed to the reaction tank 16. The isocyanate residue is temporarily stored in the residue storage tank (not shown), and thereafter, for example, recycled and/or disposed of.

In such a plant 1, a gas containing alcohol, ammonia, and carbon dioxide obtained from carbamate-forming reaction is absorbed with water, and therefore ammonia and carbon dioxide can be recovered as ammonium carbonate, and can be reused in the urea production step.

Figure 3:
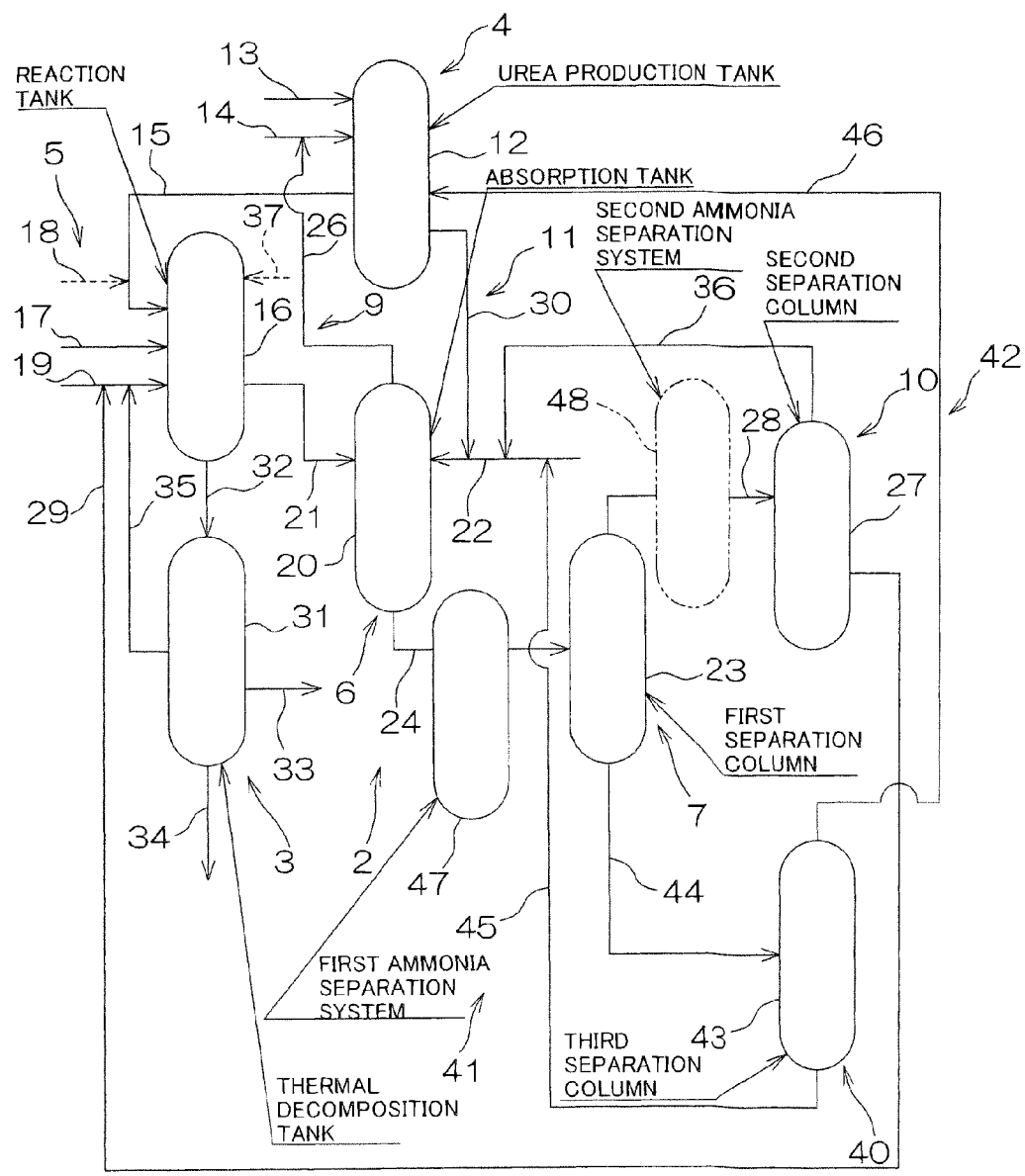
FIG. 3 is a schematic diagram illustrating the configuration of a third embodiment of a plant as a carbamate production system and an isocyanate production system in which a method for producing carbamate and a method for producing isocyanate of the present invention are used.

FIG. 3 is a schematic diagram illustrating the configuration of a third embodiment of a plant as a carbamate production system and an isocyanate production system in which a method for producing carbamate and a method for producing isocyanate of the present invention are used.

In the following, with reference to FIG. 3, the third embodiment of a plant in which the above-described method for producing carbamate and method for producing isocyanate are industrially performed, is described. Those systems and apparatuses corresponding to the above-described systems and apparatuses are designated with the same reference numerals in FIG. 3, and detailed descriptions thereof are omitted.

In the description above, the gas absorption water obtained in the absorption column 20 is directly transported to the first separation column 23, and the aqueous alcohol solution is separated from the gas absorption water in the first separation column 23; however, for example, ammonia can be separated from the gas absorption water before separating the aqueous alcohol solution.

That is, in the method described above, gas absorption water containing alcohol, ammonia, and carbon dioxide is produced in the absorption column 20, and at the same time, ammonia remained without being absorbed in water is separated; however, when the ammonia concentration of the thus obtained gas absorption water is high (e.g., more than 20 mass %), there are cases where the aqueous alcohol solution cannot be separated efficiently when the gas absorption water is fed to the first separation column 23.

To be specific, when the liquid separation column is used as the first separation column 23, and liquid-liquid separation is performed, liquid separation temperature is set to, for example, 100° C. or less, preferably, 80° C. or less, and more preferably, 40 to 70° C.

Then, when the gas absorption water fed to the first separation column 23 contains ammonia in a proportion of, for example, more than 20 mass %, particularly when carbonate is not used, a decrease in separation efficiency of aqueous alcohol solution may be caused.

Therefore, the plant 1 may further include, as shown in FIG. 3, for example, a first ammonia separation apparatus 47 as a first ammonia separation means.

The first ammonia separation apparatus 47 is interposed at a position in the first gas absorption water transporting pipe 24 in the plant 1 in order to separate ammonia from the gas absorption water, and to decrease the ammonia concentration of the gas absorption water.

For the first ammonia separation apparatus 47, for example, a known distillation column is used.

Next, description is given below of a method for production of carbamate, and production of isocyanate using the obtained carbamate with the plant 1.

In this method, in the same manner as described above, first, urea is produced in the urea production apparatus 4, and then carbamate is produced in the carbamate-forming reaction apparatus 5.

Next, in this method, in the same manner as described above, in the absorption tank 20, gas is absorbed with water, and gas absorption water is produced, and at the same time, ammonia is separated. At this time, the gas absorption water contains ammonia in a proportion of, for example, more than 20 mass %.

Then, in this method, the gas absorption water containing ammonia is pressure-transported to the first gas absorption water transporting pipe 24, and continuously fed to the first ammonia separation apparatus 47.

Then, in the first ammonia separation apparatus 47, ammonia is separated (e.g., released) and removed from the gas absorption water.

The conditions for separating ammonia are not particularly limited, and as necessary, are set appropriately.

The gas absorption water may contain ammonia even after the separation of ammonia in the first ammonia separation apparatus 47 as described above, and the ammonia concentration of the gas absorption water in such a case is, for example, 20 mass % or less, preferably 10 mass % or less, more preferably 5 mass % or less, even more preferably 3 mass % or less.

Next, in this method, the gas absorption water from which ammonia is separated is fed to the first separation column 23 (aqueous alcohol solution separation apparatus 7), and the aqueous alcohol solution is separated from the gas absorption water.

Thereafter, in this method, the gas absorption water from which the aqueous alcohol solution is separated is transported to the ammonia/carbon dioxide separation apparatus 40, an carbon dioxide gas is separated from the aqueous ammonia solution.

Then, the aqueous ammonia solution from which carbon dioxide gas is separated is fed to the ammonia separation apparatus 6 by the aqueous ammonia solution reusing apparatus 41, and used for production of gas absorption water in the ammonia separation apparatus 6. Meanwhile, the separated carbon dioxide gas is fed to the urea production apparatus 4, and used in the urea production apparatus 4.

Next, in this method, in the same manner as described above, in the second separation column 27 (alcohol reusing apparatus 10), alcohol is separated from the aqueous alcohol solution, and drained, for example, from the side portion of the column.

Thereafter, in this method, in the same manner as described above, in the thermal decomposition apparatus 3, reaction solution (reaction solution obtained by carbamate-forming reaction in the reaction tank 16) is thermally decomposed. In this fashion, isocyanate and alcohol are obtained as a decomposition solution, and isocyanate residue is obtained along with isocyanate and alcohol.

The isocyanate obtained in the same manner as described above is transported to an isocyanate purifying line, which is not shown, and the obtained alcohol is fed to the reaction tank 16. The isocyanate residue is temporarily stored in the residue storage tank (not shown), and thereafter, for example, recycled and/or disposed of.

With such a method, the ammonia contained in the gas absorption water is separated by the first ammonia separation apparatus 47, and its concentration is decreased, and therefore in the aqueous alcohol solution separation apparatus 7, the aqueous alcohol solution can be separated efficiently.

Meanwhile, in this method, as described above, the aqueous alcohol solution is separated in the first separation column 23, and transported to the second separation column 27; and the gas absorption water containing ammonia is transported to the third separation column 43. For example, the ammonia may not be separated sufficiently in the first separation column 23 and for example, the aqueous alcohol solution may contain ammonia (e.g., in a proportion of more than 10 mass %). In such a case, when the aqueous alcohol solution is fed to the second separation column 27, alcohol and water may not be separated efficiently.

To be specific, for example, when a liquid separation column is used as the second separation column 27, and liquid-liquid separation is to be performed, the liquid separation temperature is set to, for example, 100° C. or less, preferably 80° C. or less, and more preferably, 40 to 70° C.

Then, when the aqueous alcohol solution fed to the second separation column 27 contains ammonia, for example, in a proportion of more than 10 mass %, a decrease in separation efficiency of alcohol and water may be caused.

Therefore, in the plant 1, as shown in the phantom line in FIG. 3, for example, the second ammonia separation apparatus 48 as the second ammonia separation means can also be included.

The second ammonia separation apparatus 48 is interposed in the aqueous alcohol solution transporting pipe 28 in the plant 1 in order to separate ammonia from the aqueous alcohol solution, and to decrease the ammonia concentration of the aqueous alcohol solution.

For the second ammonia separation apparatus 48, the system that is the same as the above-described first ammonia separation apparatus 47 may be used.

When carbamate is produced by such a plant 1, as described above, urea is produced in the urea production apparatus 4, and then after carbamate is produced in the carbamate-forming reaction apparatus 5, gas is absorbed with water in the absorption tank 20, thereby producing gas absorption water, and separating ammonia. Thereafter, in the first ammonia separation apparatus 47, ammonia is separated from the gas absorption water, and the gas absorption water from which the ammonia is separated is fed to the first separation column 23 (aqueous alcohol solution separation apparatus 7), and the aqueous alcohol solution is separated from the gas absorption water.

In this method, the aqueous alcohol solution drained from the first separation column 23 contains ammonia, for example, in a proportion of more than 10 mass %, and such an aqueous alcohol solution is pressure-transported to the aqueous alcohol solution transporting pipe 28, and continuously fed to the second ammonia separation apparatus 48.

Then, in the second ammonia separation apparatus 48, ammonia is separated (e.g., released) and removed from the aqueous alcohol solution.

The conditions for separating ammonia are not particularly limited, and as necessary, are set appropriately.

The aqueous alcohol solution may contain ammonia even after the separation of ammonia in the second ammonia separation apparatus 48 as described above, and the ammonia concentration of the aqueous alcohol solution in such a case is, for example, 10 mass % or less, preferably 5 mass % or less, more preferably 3 mass % or less, and even more preferably 1 mass % or less.

Next, in this method, in the same manner as described above, in the second separation column 27 (alcohol reusing apparatus 10), alcohol is separated from aqueous alcohol solution from which ammonia is separated, and drained, for example, from the side portion of the column.

Thereafter, in this method, in the same manner as described above, in the thermal decomposition apparatus 3, reaction solution (reaction solution obtained by carbamate-forming reaction in the reaction tank 16) is thermally decomposed. In this fashion, isocyanate and alcohol are obtained as a decomposition solution, and isocyanate residue is obtained along with isocyanate and alcohol.

The isocyanate obtained in the same manner as described above is transported to an isocyanate purifying line, which is not shown, and the obtained alcohol is fed to the reaction tank 16. The isocyanate residue is temporarily stored in the residue storage tank (not shown), and thereafter, for example, recycled and/or disposed of.

With such a method, ammonia contained in the aqueous alcohol solution is separated by the second ammonia separation apparatus 48, and its concentration is decreased, and therefore in the second separation column 27, alcohol and water can be separated efficiently from the aqueous alcohol solution.

In the description above, the first separation column 23 and the second separation column 27 are used to separate alcohol from the gas absorption water; however, the number of separation columns that separate alcohol is not particularly limited, and as in the above-described first ammonia separation apparatus 47 and the second ammonia separation apparatus 48, the ammonia separation apparatus can be provided upstream of the separation column so as to form a pair with the separation column.

In such a case, preferably, ammonia is separated (released) in the ammonia separation apparatus provided immediately before the separation column (the last stage separation column) that separates alcohol lastly so that the ammonia concentration in the solution is 10 mass % or less.

A method for producing carbamate and a production system thereof, and a method for producing isocyanate and a production system thereof are described above. Such a plant 1 may include, as necessary, at a suitable position, a pretreatment system for performing pretreatment steps such as a dehydration step; and a post treatment system for performing an intermediate step, a distillation step, a filter step, a purification step, and a recovery step.

While the illustrative embodiments of the present invention are provided in the above description, such is for illustrative purpose only and it is not to be construed restrictively. Modification and variation of the present invention that will be obvious to those skilled in the art is to be covered by the following claims.

Industrial Applicability

A method for producing carbamate of the present invention and a production system thereof can be used for production of carbamate, which is useful as a raw material for isocyanate, which is a raw material for polyurethane.

Furthermore, a method for producing isocyanate of the present invention and a production system thereof can be used for production of isocyanate, which is useful as a raw material for polyurethane.

The invention claimed is:

1. A method for producing carbamate, the method comprising the steps of:
    a urea production step of producing urea by reaction between ammonia and carbon dioxide gas,
    a carbamate-forming step of producing carbamate by carbamate-forming reaction between amine, the urea, and alcohol, and by-producing a gas containing alcohol, ammonia, and carbon dioxide,
    an ammonia separation step of absorbing the gas with water to produce a gas absorption water, and separating ammonia,
    an aqueous alcohol solution separation step of separating an aqueous alcohol solution from the gas absorption water,
    an ammonia/carbon dioxide separation step of separating carbon dioxide gas from the aqueous ammonia solution in the gas absorption water from which the aqueous alcohol solution is separated, and
    an aqueous ammonia solution reusing step of using the aqueous ammonia solution along with the water for production of the gas absorption water.

2. The method for producing carbamate according to claim 1, wherein
    in the ammonia separation step, the gas is absorbed with the water in the presence of carbonate,
    in the ammonia/carbon dioxide separation step, carbon dioxide gas is separated from the aqueous ammonia solution in the presence of the carbonate, and
    in the aqueous ammonia solution reusing step, along with the aqueous ammonia solution and the water, the carbonate is used for production of the gas absorption water.

3. The method for producing carbamate according to claim 1, further comprising a step of:
    a carbon dioxide gas reusing step of recovering the carbon dioxide gas separated in the ammonia/carbon dioxide separation step, and using the carbon dioxide gas in the urea production step.

4. The method for producing carbamate according to claim 1, further comprising a step of:
    an ammonia reusing step of using, in the urea production step, the ammonia separated in the ammonia separation step.

5. The method for producing carbamate according to claim 1, further comprising a step of:
    an alcohol reusing step of separating alcohol from the aqueous alcohol solution and using the alcohol in the carbamate-forming step.

6. The method for producing carbamate according to claim 1, further comprising a step of:
    a water reusing step of using, in the ammonia separation step, water drained in the urea production step.

7. A method for producing isocyanate comprising a carbamate production step of producing carbamate by a method for producing carbamate, and an isocyanate production step of producing isocyanate by thermally decomposing the obtained carbamate, the method for producing carbamate comprising the steps of:

a urea production step of producing urea by reaction between ammonia and carbon dioxide gas, a carbamate-forming step of producing carbamate by carbamate-forming reaction between amine, the urea, and alcohol, and by-producing a gas containing alcohol, ammonia, and carbon dioxide, an ammonia separation step of absorbing the gas with water to produce a gas absorption water, and separating ammonia, an aqueous alcohol solution separation step of separating an aqueous alcohol solution from the gas absorption water, an ammonia/carbon dioxide separation step of separating carbon dioxide gas from the aqueous ammonia solution in the gas absorption water from which the aqueous alcohol solution is separated, and an aqueous ammonia solution reusing step of using the aqueous ammonia solution along with the water for production of the gas absorption water.

* * * * *